US011980701B2

(12) United States Patent
Hotchkiss et al.

(10) Patent No.: US 11,980,701 B2
(45) Date of Patent: May 14, 2024

(54) JOINT IMPLANT WITH CONSTANT AND CONTINUOUS RELEASE OF THERAPEUTIC AGENT

(71) Applicant: Diffusion RX, Inc., Riverside, CT (US)

(72) Inventors: Robert N. Hotchkiss, Riverside, CT (US); Paul Ashton, San Diego, CA (US); Martin Nazzaro, Quincy, MA (US)

(73) Assignee: Diffusion RX, Inc., Riverside, CT (US)

( * ) Notice: Subject to any disclaimer, the term of this patent is extended or adjusted under 35 U.S.C. 154(b) by 0 days.

(21) Appl. No.: 17/576,635

(22) Filed: Jan. 14, 2022

(65) Prior Publication Data

US 2022/0226544 A1 Jul. 21, 2022

Related U.S. Application Data

(60) Provisional application No. 63/138,094, filed on Jan. 15, 2021.

(51) Int. Cl.
*A61L 27/54* (2006.01)
*A61F 2/28* (2006.01)
(Continued)

(52) U.S. Cl.
CPC ............... *A61L 27/54* (2013.01); *A61F 2/28* (2013.01); *A61K 31/573* (2013.01); *A61L 27/06* (2013.01);
(Continued)

(58) Field of Classification Search
CPC .......... A61M 31/002; A61B 2017/561; A61B 17/864; A61F 2002/3021;
(Continued)

(56) References Cited

U.S. PATENT DOCUMENTS 6,196,993 B1 * 3/2001 Cohan ................... A61F 9/0017
604/93.01
8,747,440 B2 6/2014 Yue
(Continued)

OTHER PUBLICATIONS

International Search Report and Written Opinion for International Application No. PCT/US2022/012550 dated Apr. 8, 2022.

*Primary Examiner* — Javier G Blanco
(74) *Attorney, Agent, or Firm* — Dechert LLP; Andrea L. C. Reid; Sean M. Coughlin

(57) ABSTRACT

Provided herein are devices and methods for treating inflammation and pain of articular joints (e.g., the knee). An implantable device includes an elongate body extending from a proximal end to a distal end, a flange disposed at the proximal end, a bore extending from an opening at the proximal end into the elongate body, one or more fixation members disposed on an outer surface of the elongate body, and a payload (e.g., a drug-polymer core) having a therapeutic agent disposed within the bore. The payload has a substantially constant surface area on an exposed portion throughout elution of the therapeutic agent after the implantable device is implanted in a body. The therapeutic agent is configured to elute using zero-order kinetics, constantly and continuously at an amount that is above a predetermined lower threshold and does not exceed a predetermined upper threshold unlike a pulse-dose injection.

36 Claims, 26 Drawing Sheets

(51) Int. Cl.
*A61F 2/30* (2006.01)
*A61K 31/573* (2006.01)
*A61L 27/06* (2006.01)
*A61L 27/18* (2006.01)

(52) U.S. Cl.
CPC ....... *A61L 27/18* (2013.01); *A61F 2002/2825* (2013.01); *A61F 2002/3021* (2013.01); *A61F 2002/30593* (2013.01); *A61F 2002/3085* (2013.01); *A61F 2002/30884* (2013.01); *A61F 2310/00023* (2013.01); *A61L 2430/02* (2013.01); *A61L 2430/24* (2013.01)

(58) Field of Classification Search
CPC .... A61F 2002/3085; A61F 2002/30884; A61F 2002/3068; A61F 2002/2825; A61L 27/54
See application file for complete search history.

(56) References Cited

U.S. PATENT DOCUMENTS

| | | | |
|---|---|---|---|
| 9,545,311 B2* | 1/2017 | Courtney, Jr | A61F 2/4081 |
| 2004/0180072 A1* | 9/2004 | Tunc | A61L 27/18 514/304 |
| 2005/0031665 A1 | 2/2005 | Watson et al. | |
| 2005/0228388 A1 | 10/2005 | Brodke et al. | |
| 2007/0298075 A1* | 12/2007 | Borgia | A61M 31/002 424/428 |
| 2010/0042214 A1* | 2/2010 | Nebosky | A61F 2/36 604/93.01 |
| 2011/0093008 A1* | 4/2011 | Mayer | A61N 7/00 606/213 |
| 2011/0238016 A1 | 9/2011 | Hotchkiss et al. | |
| 2012/0059338 A1* | 3/2012 | Beeley | A61F 9/00772 604/294 |
| 2019/0167325 A1 | 6/2019 | Armbruster et al. | |

* cited by examiner

SECTION A-A

Potentially longer lasting

| Treatment | Median effectiveness |
|---|---|
| NSAID (Non-steroidal anti-inflammatory drug, e.g. Advil) | • Four to eight hours[1] |
| Hyaluronic acid injection (e.g. Euflexxa) | • Eight to ten weeks[2] |
| Cortisone shot (e.g. Kenalog) | • Six to twelve weeks[3] |
| Zilretta (Flexion Therapeutics) | • 12 weeks |
| Diffusion Rx (based on initial Phase I trials) | • 26 weeks (52 weeks for next phase) |

Fig. 5A

JOINT IMPLANT WITH CONSTANT AND CONTINUOUS RELEASE OF THERAPEUTIC AGENT

This application claims the benefit of U.S. Provisional Application No. 63/138,094, filed on Jan. 15, 2021, which is hereby incorporated by reference in its entirety.

FIELD OF THE INVENTION

Embodiments of the present disclosure generally relate to implants for treatment of articular joint conditions (e.g., arthritis) that directly expose synovial tissue and its constituent cells to an effective therapeutic agent at a therapeutically-effective concentration with constant and continuous elution, sustained for a year or longer, after percutaneous (e.g., minimally-invasive) insertion of the implant.

BACKGROUND

As human life expectancy increases due to advances in medicine (e.g. in treatment and prevention of heart disease and cancer), inflammation and painful deterioration of articular joints from, e.g., arthritis, has become a front-and-center issue throughout the world. Average life expectancy has risen from the mid-60 s in 1960 to a projected age in the mid-80s by 2030. Along with the expanding cohort, habitual physical activity and exercise, once regarded as an optional virtue, is now deemed a requirement for reducing obesity, improving cognitive skills, and contributing to general well-being. The demand on the joints—specifically the hips, knees, shoulders, and elbows—is not just due to increased longevity, but also a higher intensity of activity throughout our lives.

A source of inflammation in an ageing joint—specifically, one not afflicted by an autoimmune disease (such as rheumatoid arthritis)—is the patient's own physiology at work due the natural process of ageing. The synovial lining of the joint provides a myriad of functions in support of the health of articular cartilage. In particular, the synovial lining and its constituent cells, called the "synoviocytes" (which are not a uniform population), permit nutrients to pass from the blood stream to the cartilage and synthesizes proteoglycans, among many other molecules, that support cartilage health. There is also a "cleaning and clearing" function that becomes more active with ageing as the cartilage breaks down into fragments and wear particles. As these fragments are trapped and digested by the phagocytic synoviocytes, a variety of cytokines and proinflammatory molecules are released, thereby causing pain, swelling, and further destruction of the joint. To date, most therapeutic measures used are designed to deliver an anti-inflammatory agent to quell this activity.

One method to reduce inflammation is to administer oral non-steroidal anti-inflammatory drugs (NSAIDs). NSAIDs, after ingestion, reach the synovium by diffusing from the blood stream (plasma) into the joint. In some instances, opioids are prescribed to a patient experiencing painful joints; however, opioid consumption is a dangerous alternative except in the most acute setting. Once NSAID medication loses its effectiveness, steroid (e.g., glucocorticoid) injections are often used intermittently on a limited basis. Steroid injections have been used to treat knee pain and inflammation since the 1950s. The single intra-articular injection provides excellent relief but is short-lived because it is a pulse-dose of a soluble compound that diffuses across the synovial membrane and into the blood stream in a matter of days with logarithmic decay. Recently, glucocorticoid has been embedded in a polymeric microsphere (e.g., triamcinolone acetonide extended-release injectable suspension) in order to extend the time of exposure of the inflamed synovium to the glucocorticoid. As microspheres dissolve, the surface area of the sphere—$4\pi r^2$—decreases logarithmically as does the amount of drug eluted from the sphere. However, while the synovial lining and the cells are exposed to a slightly longer duration due to the slow dissolving microspheres, the duration of exposure is marginally extended by a few weeks and may not have a meaningful impact on the number of visits to a healthcare provider for treatment (e.g., steroid injections).

Glucocorticoids generally work by blocking, inhibiting, or neutralizing the inflammatory, destructive cell activity of the synovial cells. In 2018, approximately 5.4 million Americans spent about $4.7 billion on intra-articular injections for knee osteoarthritis annually. The breakdown of injections is as follows: ~4.5 million Americans receive steroid injections at a total cost of ~$3.2 billion assuming 1.5 treatments per year and 4 injections per treatment at $120 per injection; ~0.9 million Americans receive hyaluronic acid injections at a total cost of ~$1.3 billion assuming 1.3 treatments per year and 3.5 injections per treatment at $310 per injection; and ~0.1 million Americans receive triamcinolone acetonide extended-release injectable suspension injections at a total cost of ~$0.2 billion assuming 2.5 treatments per year and $570 per treatment.

No matter the route of administration, the target of the anti-inflammatory class of medications is the synovial lining of the joint. The synoviocyte, consisting of several cell types, exacerbates damaging and pain-causing inflammatory cytokines in response to ongoing cartilage fibrillation in osteoarthritis or an autoimmune stimulus in rheumatoid arthritis. The benefit of corticosteroid treatment to suppress the synovial inflammatory reaction is well-established, but the remaining challenge is how to sustain a therapeutically-effective level of a therapeutic agent (e.g., glucocorticoid) at a constant and continuous, sub-toxic concentration.

Other methods of treating articular joint pain caused by inflammatory conditions may include periodic injections of hyaluronic acid and/or platelet-rich plasma. However, all of these methods of treating inflammatory conditions require frequent injections and do not maintain a constant and continuous, therapeutically-effective amount of active drug in the intra-articular space over long periods of time (e.g., at least a year) because they are administered as pulse-doses, which decrease logarithmically over time.

Accordingly, there is a need for an implantable device that provides constant and continuous release of a therapeutic agent within the body (e.g., an intra-articular space) over long periods of time. In particular, a need exists for a device that can deliver effective synovial exposure of a proven glucocorticoid for a year or greater and eliminate the need for pulse-dosing larger doses (by several orders of magnitude) of systemic steroid required by the prior methods of delivery.

BRIEF SUMMARY

In various embodiments, an implantable device includes an elongate body extending from a proximal end to a distal end, a flange disposed at the proximal end, a bore extending from an opening at the proximal end into the elongate body, one or more fixation members disposed on an outer surface of the elongate body, and a payload disposed within the bore. The payload includes a therapeutic agent configured to elute constantly and continuously over a predetermined time period and a substantially constant surface area on an exposed portion of the payload throughout elution.

In various embodiments, the implantable device further includes one or more interference rings disposed along the elongate body. In various embodiments, the implantable device further includes two or more wing tabs disposed along the elongate body. In various embodiments, the two or more wing tabs are disposed opposite one another. In various embodiments, the implantable device further includes threads disposed along the elongate body. In various embodiments, the distal end comprises a conical shape. In various embodiments, the distal end comprises a frustoconical shape. In various embodiments, a length from the proximal end to the distal end is about 7 mm to about 12 mm. In various embodiments, the bore comprises a depth of about 0.5 mm to about 12 mm. In various embodiments, a diameter of the bore is about 0.5 mm to about 9.5 mm. In various embodiments, the bore extends only partially into the elongate body. In various embodiments, the elongate body has a first diameter and the flange has a second diameter. In various embodiments, the second diameter is larger than the first diameter. In various embodiments, the first diameter is about 1.0 mm to about 10.0 mm. In various embodiments, the second diameter is about 1.25 mm to about 12.0 mm. In various embodiments, the payload is in direct contact with an inner surface of the bore. In various embodiments, the substantially constant surface area of the exposed portion of the payload is substantially planar with a plane of the flange throughout elution. In various embodiments, the payload is configured to elute constantly and continuously for about six months. In various embodiments, the payload is configured to elute the therapeutic agent constantly and continuously for about seven months. In various embodiments, the payload is configured to elute the therapeutic agent constantly and continuously for about eight months. In various embodiments, the payload is configured to elute the therapeutic agent constantly and continuously for about nine months. In various embodiments, the payload is configured to elute the therapeutic agent constantly and continuously for about ten months. In various embodiments, the payload is configured to elute the therapeutic agent constantly and continuously for about eleven months. In various embodiments, the payload is configured to elute the therapeutic agent constantly and continuously for about a year. In various embodiments, the payload is configured to elute the therapeutic agent constantly and continuously for at least a year. In various embodiments, the therapeutic agent includes a corticosteroid. In various embodiments, the corticosteroid includes dexamethasone. In various embodiments, the elongate body includes titanium. In various embodiments, the elongate body includes polyetherketonketone (PEKK). In various embodiments, the elongate body includes polyether ether ketone (PEEK). In various embodiments, the elongate body comprises a bone anchor.

In various embodiments, a method of treating an inflammatory condition includes implanting an implantable device into a bone, thereby allowing the payload to elute the therapeutic agent into an intra-articular space at a constant and continuous rate for at least a year. In various embodiments, the implantable device includes an elongate body extending from a proximal end to a distal end, a flange disposed at the proximal end, a bore extending from an opening at the proximal end into the elongate body, one or more fixation members disposed on an outer surface of the elongate body, and a therapeutic agent disposed within the bore. The therapeutic agent includes a substantially constant surface area on an exposed portion throughout elution. In various embodiments, the therapeutic agent is configured to elute constantly and continuously at an amount that is above a predetermined lower threshold and does not exceed a predetermined upper threshold. In various embodiments, the predetermined upper threshold is associated with negative effects on one or more bodily tissues.

In various embodiments, a method of treating an inflammatory condition includes providing an implantable device, forming a hole in a bone, and inserting the implantable device into the formed hole thereby securing the implantable device in the bone. In various embodiments, the implantable device includes an elongate body extending from a proximal end to a distal end, a flange disposed at the proximal end, a bore extending from an opening at the proximal end into the elongate body, one or more fixation members disposed on an outer surface of the elongate body, and a therapeutic agent disposed within the bore. The therapeutic agent includes a substantially constant surface area on an exposed portion throughout elution.

In various embodiments, the hole is formed using a drill. In various embodiments, the hole has a depth of about 8 mm to about 16 mm. In various embodiments, the hole has a depth of about 12 mm. In various embodiments, the hole is formed in a non-load-bearing portion of the bone. In various embodiments, the bone is a femur. In various embodiments, the hole is formed in a periarticular region.

BRIEF DESCRIPTION OF THE SEVERAL VIEWS OF THE DRAWINGS

FIG. 5A illustrates a table of treatments and length of effectiveness in accordance with an embodiment of the present disclosure.

DETAILED DESCRIPTION

Figure 1A:
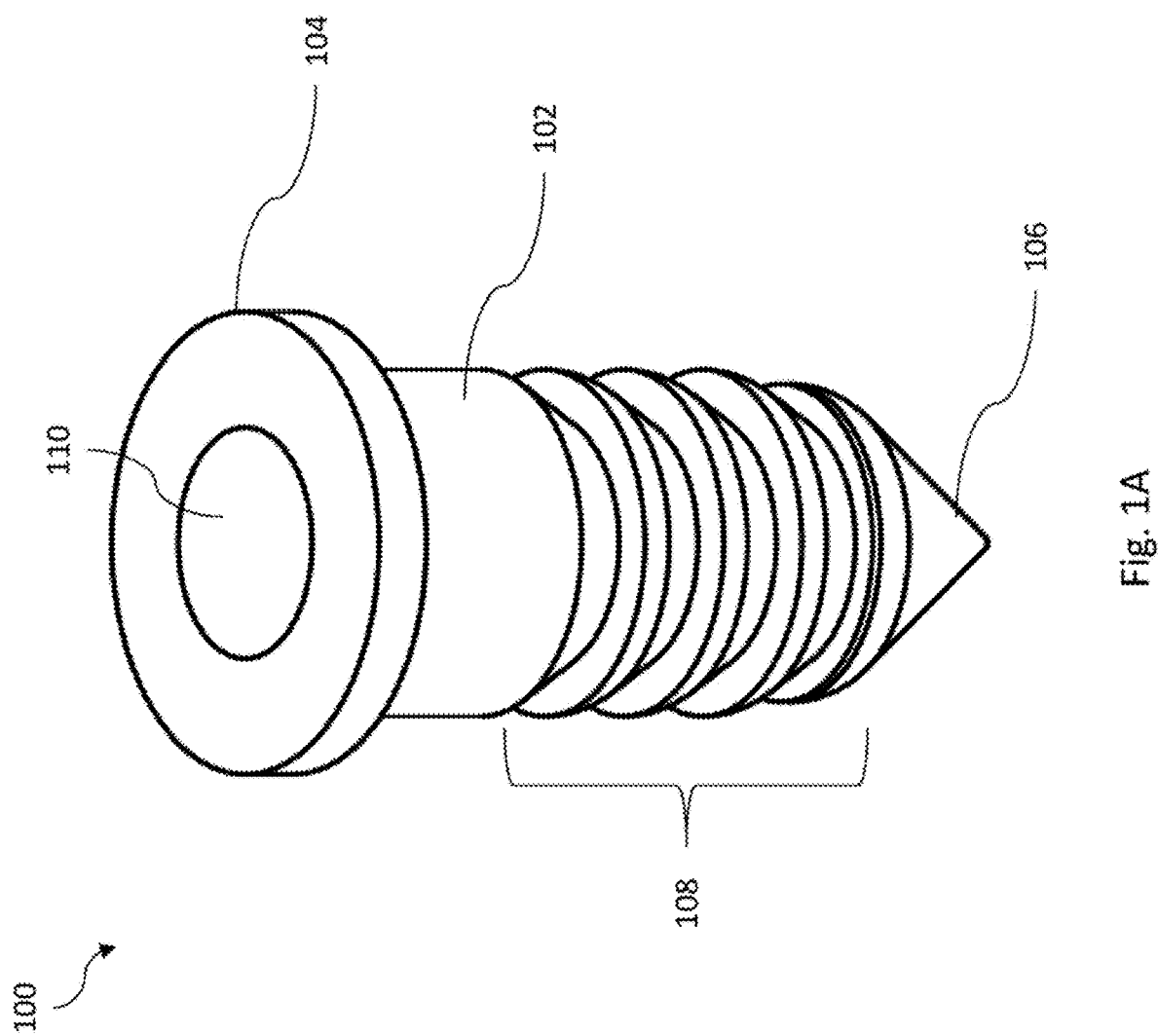
FIGS. 1A-1C illustrate an implant configured for constant, continuous, and controlled drug delivery in accordance with an embodiment of the present disclosure.

The present disclosure generally relates to the treatment of conditions of the articular joint, such as the knee, by directly exposing the synovial layer, the primary target tissue of these conditions, to compounds of known efficacy using an implanted device. In many conditions of the joint, the optimal dose or exposure of the synovial layer to the drug is a near constant and continuous—requiring a zero-order kinetic release.

In various embodiments, the dose and level of therapeutic agent delivered by the implantable devices of the present disclosure is continuous and operates as a zero-order kinetic release thus exposing the target tissue at a level above the minimal effective level and below a concentration or exposure that could be toxic or have harmful effects.

The implantable devices of the present disclosure achieve a zero-order kinetic delivery by using a drug-polymer core that, by designing geometry and specific features of the external housing, exposes a single plane of the drug-polymer core to the eluting synovial fluid. The drug-polymer core may be bioerodible. Once the drug is released from the drug-polymer core elution surface, the drug diffuses and is taken up by the synoviocytes and the other constituent cells of the synovial membrane. This single-plane surface erosion thus achieves zero-order kinetic drug delivery in articulating joints. A constant therapeutic level of drug may be maintained up to a year at a level above the minimum therapeutic exposure but below local or systemic toxicity.

Degenerative arthritis is generally treated via a steroid (e.g., glucocorticoid) injection to specifically suppress or extinguish local inflammation and the damaging cytokines. However, a single injection of a steroid compound alone or combined with a dissolving microsphere for extended release, nonetheless displays a first-order kinetics—a logarithmic pattern of drug delivery and synovial exposure.

The drug levels locally and systemically, because of first-order kinetics, must first exceed the therapeutic threshold needed to suppress or extinguish the inflammatory response. With logarithmic decline, the level of drug then drops below the minimal therapeutic exposure (MTE) within days or weeks. Though intra-articular injection is, in most cases, preferable to oral or parenteral (intramuscular or intravenous) dosing because even higher levels of drug are required to achieve the minimal therapeutic exposure in the joint.

The therapeutic benefit may exceed the actual presence of drug, but once the suppression effect of the steroid is gone, inflammation may recur since the fragmentation and fibrillation of cartilage continues unabated due to mechanical wear with activity and age. The injections then need to be repeated, which requires reexamination, imaging, and/or another visit to an outpatient facility.

Recently, glucocorticoid has been imbedded in a polymeric microsphere in order to extend the time of exposure of the inflamed synovium to the glucocorticoid. However, while the synovial lining and the cells are exposed to a slightly longer duration, the duration is extended by only a few months and still exhibits the logarithmic profile.

No matter the route of administration, the target of the anti-inflammatory class of medications is the synovial lining of the joint. The synoviocyte consists of several cell types, which can collectively enhance damaging and pain-causing inflammatory cytokines in response to ongoing cartilage fibrillation in osteoarthritis or an autoimmune stimulus in rheumatoid arthritis. The benefit of corticosteroid treatment to suppress the synovial inflammatory reaction is well-established, but the remaining challenge is how to sustain an effective therapeutic level of the agent at a constant and continuous sub-toxic concentration.

Accordingly, presented herein is a device that because of its design (including component parts and geometry) and its specific anatomic localization, can deliver an effective synovial exposure of a proven glucocorticoid for a year or greater and eliminate the need for pulse-dosing, which is associated with higher—by several orders of magnitude—synovial steroid exposure and/or increased risk of local or even systemic toxicity.

In various embodiments, an implantable device described herein includes an elongate body having a flange at a proximal end. In various embodiments, the distal end may be shaped to aid insertion into a tissue (e.g., bone). In various embodiments, the device includes a bore extending from an opening at a proximal end of the device and partially through the elongate body. In various embodiments, a payload may be disposed within the bore. In various embodiments, the payload may include a drug-polymer core. As used herein, a "therapeutic drug-polymer core", "drug-polymer core," or "therapeutic-polymer core" refers to a therapeutic drug disposed within a polymer matrix that is placed within the bore of the implant. In various embodiments, the polymer matrix may be biodegradable. In various embodiments, the polymer matrix may be erodible. In various embodiments, the polymer matrix may be non-biodegradable. In various embodiments, the drug-polymer core may have a substantially constant and substantially continuous elution profile of therapeutic agent to thereby provide surrounding tissue with a constant and continuous amount of the therapeutic agent.

As used herein, the terms "drug" or "therapeutic agent" are intended to refer to any suitable biologic, drugs, and/or pharmaceutical compounds, as well as any other drugs, pharmaceutical compounds, or other substances, in any useful combination, for obtaining a therapeutic effect by delivery via the sustained-release implantable devices described herein, unless a different meaning is explicitly indicated.

In various embodiments, the implantable device may be inserted, by a percutaneous procedure, into a specific area of the joint that is referred to as an "optimal safe zone" (OSZ). In various embodiments, the device may be inserted and lodged into the optimal safe zone after identifying the optimal position using, but not limited to, radiologic (e.g., fluoroscopic, MRI, CT, etc.) guidance. In various embodiments, other safe-zone mapping technologies in development may be used. In various embodiments, a properly sized hole may be formed by drilling to accommodate the housing-payload combination through a trocar technique and cannulated drill system. In various embodiments, the device may be inserted and remains at the proper, effective position by implant design (e.g., the lip of the device and the depth control of the drill prevent sinking it below the outer cortex of the bone). In various embodiments, the geometry of the payload drug-polymer may include any suitable shape, such as, for example, a cylindrical shape. In various embodiments, other suitable shapes may be used. In various embodiments, the drug-polymer is exposed to the synovial fluid in the immediate area surrounding the implant and the elution of the polymer and release of the compound, a glucocorticoid for example (but not limited to) is diffused into the joint in the manner of a dissolution-based matrix.

In various embodiments, because only the surface of the drug-polymer core (e.g., a cylinder) is exposed to synovial fluid, a constant amount of therapeutic agent may be released (e.g., via erosion of the drug-polymer core thereby releasing therapeutic agent contained therein), as release is proportional to the area of the exposed end. In various embodiments, the area of the exposed portion is about equal to $\pi r^2$. In various embodiments, limiting drug-polymer core surface exposure by virtue of the impervious housing in the elongate body and maintaining the constant area of the exposed portion ensures a substantially constant dissolution of the drug-polymer matrix and a controlled, consistent, and constant release of glucocorticoid (or other therapeutic agent). In various embodiments, the geometry of the payload portion can be altered to suit the optimal dosing requirements of the clinical need with or without changing the shape of the outer housing. In various embodiments, the duration of release can range from a few months to over a year. For example, a variable-shaped (e.g., a cone-shaped or pyramid-shaped) payload can be made such that the end having a smaller area of the shape representing the bottom of the drug-polymer core so that the release rate decreases over time. Alternatively, the variable-shaped (e.g., a cone-shaped or pyramid-shaped) payload can be made such that the end having a smaller area of the shape representing the top of the drug-polymer core so that the release rate increases over time. In various embodiments, the drug-polymer core may be cube-shaped. In various embodiments, the variable-shaped payload may include a shape that includes two or more sections of varying cross-section. For example, the variable-shaped payload may include two cones connected at the respective bases, such that the release rate increases over time to a peak rate (where the two bases contact one another) and then decreases over time.

Figure 1B:
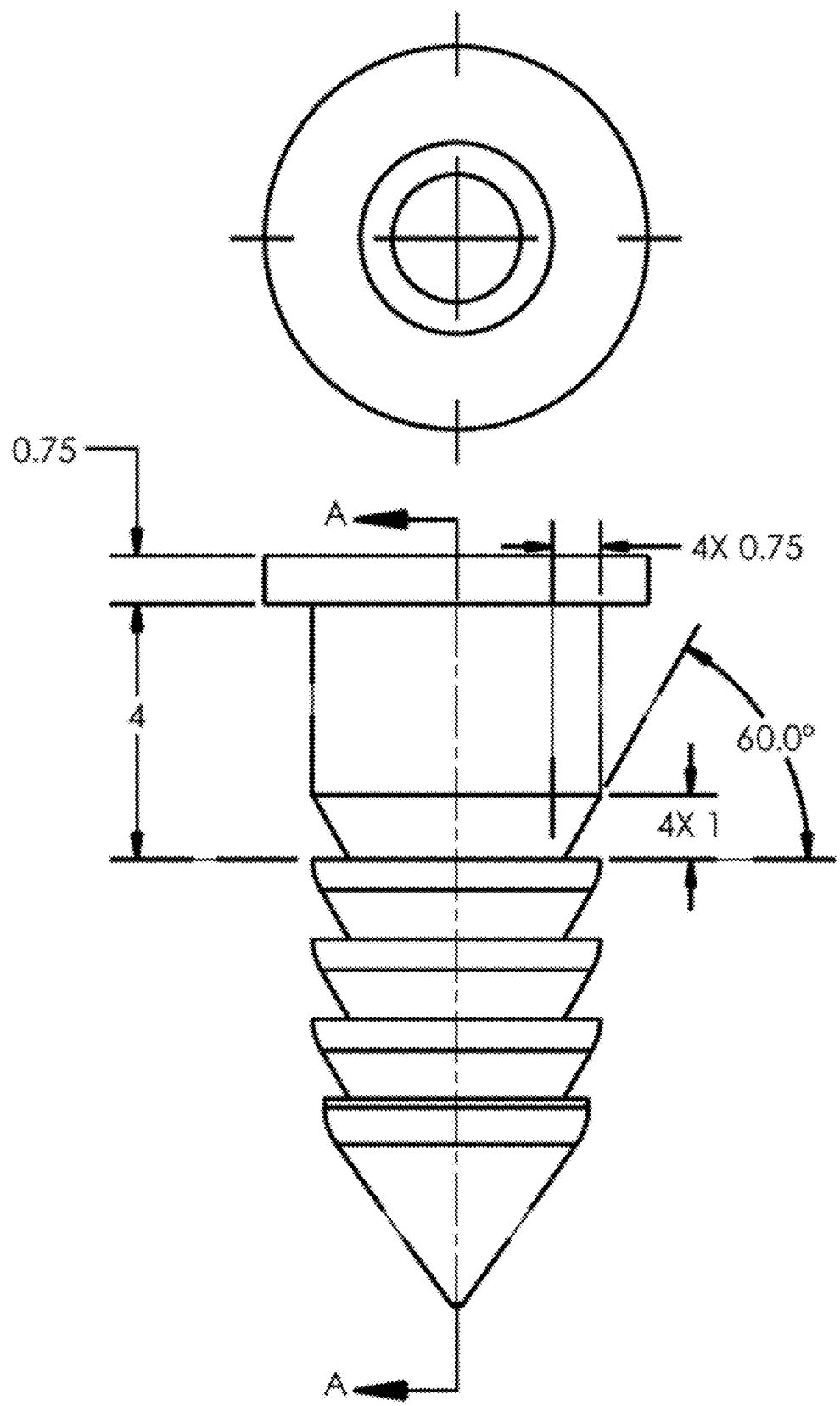
Figure 1C:
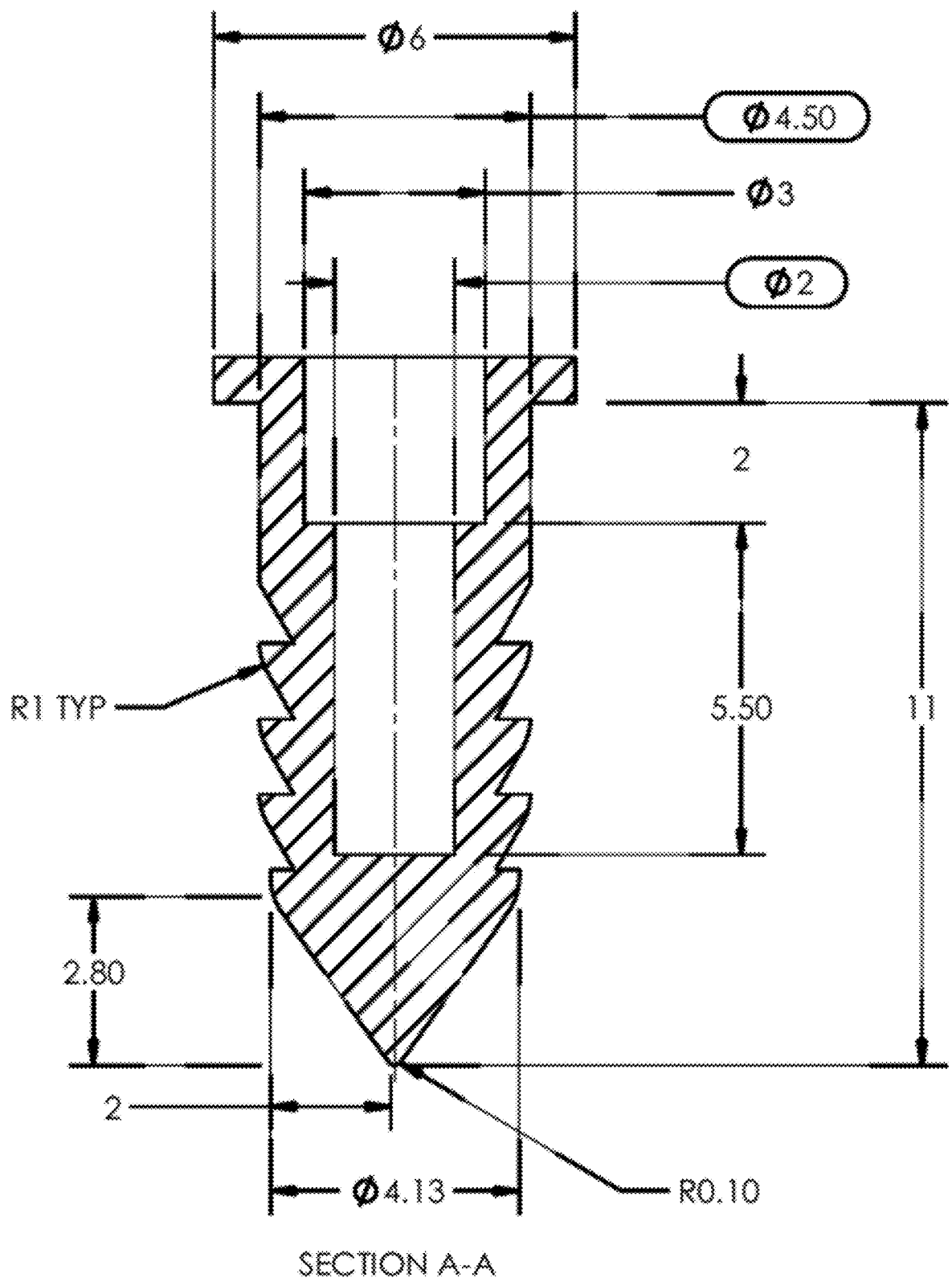

FIGS. 1A-1C illustrate an implant 100 configured for constant, continuous, and controlled drug delivery. The implant 100 includes an elongate body 102 extending from a proximal end 104 to a distal end 106. In various embodiments, the proximal end 104 includes a flange extending radially outward from the elongate body 102. In various embodiments, the flange prevents the implant from being inserted too deep in the bone. In various embodiments, the elongate body 102 include a first width (e.g. diameter). In various embodiments, the diameter of the elongate body may be about 1.0 mm to about 10.0 mm. In various embodiments, the flange may include a second width (e.g., diameter) that is larger than the first diameter. In various embodiments, the second diameter may be about 1.25 mm to about 12.0 mm. In various embodiments, the flange extends about 0.25 mm radially outward from the elongate body 102. Preferably, the second diameter may be about 3.0 mm to about 8.0 mm. In various embodiments, the second diameter may be about 1.0 mm or less. In various embodiment, the second diameter may be 1.0 cm or more. In various embodiments, the second diameter may be about 1.5 cm. In various embodiments, the distal end 106 includes a conical shape having a pointed (e.g., sharpened) end. In various embodiments, the distal end 106 may be blunt (i.e., not pointed). In various embodiments, the elongate body may include one or more interference rings 108 configured to secure the implant within a tissue (e.g., bone). In various embodiments, the diameter can be adjusted based on the desired release rate of the drug, the anatomical site, and the nature of the procedure.

In various embodiments, the implant 100 further includes a bore 110 extending from the proximal end 104 at least partially into the elongate body 102. In various embodiments, the bore 110 may include a third diameter that is smaller than the first diameter. In various embodiments, the third diameter may be about 0.5 mm to about 8.0 mm. In some embodiments, the bore 110 can be configured with a single radius such that the bore is a uniformly-shaped cavity extending from the bottom of the bore to the opening at the proximal end 104 of the implant. In various embodiments, the bore 110 may have a varying diameter along its longitudinal axis. In various embodiments, the larger width may be about 1.0 mm to about 15.0 mm. In various embodiments, the larger width may be 1.0 cm or more. In various embodiments, the larger width may be 1.5 cm or more. In various embodiments, a payload (e.g., a drug-polymer core) may be disposed within the bore. In various embodiments, once implanted into the body, the payload may be configured to elute a therapeutic agent into an area surrounding the implant constantly and continuously over a long period of time. In various embodiments, the payload may elute therapeutic agent for 6 months or more. In various embodiments, the payload may elute therapeutic agent for 7 months or more. In various embodiments, the payload may elute therapeutic agent for 8 months or more. In various embodiments, the payload may elute therapeutic agent for 9 months or more. In various embodiments, the payload may elute therapeutic agent for 10 months or more. In various embodiments, the payload may elute therapeutic agent for 11 months or more. In various embodiments, the payload may elute therapeutic agent for a year or more. In various embodiments, the payload may elute therapeutic agent for about 1 year. In various embodiments, the payload may elute therapeutic agent for about 18 months. In various embodiments, the diameter of the bore 110 may be up to 1 mm less than the second diameter of the proximal end 104 (representing the perimeter of the flange). In various embodiments, depending on the shape of the implant and/or the drug-polymer core, the diameter of the bore may be up to 1 mm less than the first diameter (representing the outer perimeter of the elongate body 102). Preferably, the diameter of the bore 110 is about 1.0 mm to 2.0 mm less than the second diameter.

In various embodiments, the therapeutic agent may include a corticosteroid. In various embodiments, the corticosteroid may be a glucocorticoid. In various embodiments, the corticosteroid may be a mineralocorticoid. In various embodiments, the therapeutic agent may include methylprednisolone, dexamethasone, dexamethasone sodium phosphate, hydrocortisone, betamethasone, prednisolone, and/or triamcinolone. In various embodiments, the therapeutic agent may be a NSAID. In various embodiments, the therapeutic agent may be an anti-inflammatory drug.

Specific types of therapeutic agents include, either directly or after appropriate modification, without limitation: anti-angiogenesis factors, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; inflammasome inhibitor; antinauseants; antineoplastics; antiparkinsonism drugs; antiproliferatives; antimitotics; antimetabolite compounds; angiostatics; angiostatic steroids; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; catecholamines; diuretics; vasodilators including general coronary, peripheral and cerebral; central nervous system stimulants; cough and cold preparations, including decongestants; growth factors, hormones such as estradiol and other steroids, including corticosteroids; hypnotics; immunosuppressives; steroids; corticosteroids; glucocorticoids; muscle relaxants; parasympatholytics; psychostimulants; sedatives; and tranquilizers; and naturally derived or genetically engineered proteins, polysaccharides, glycoproteins, lipoproteins, interferons, cytokines, chemotherapeutic agents and other anti-neoplastics, antibiotics, anti-virals, anti-fungals, anti-inflammatories, anticoagulants, lymphokines, or antigenic materials. U.S. Pat. No. 7,976,858 describes various types of therapeutic drugs that may be included in implantable devices, which is hereby incorporated by reference herein in its entirety.

Figure 2A:
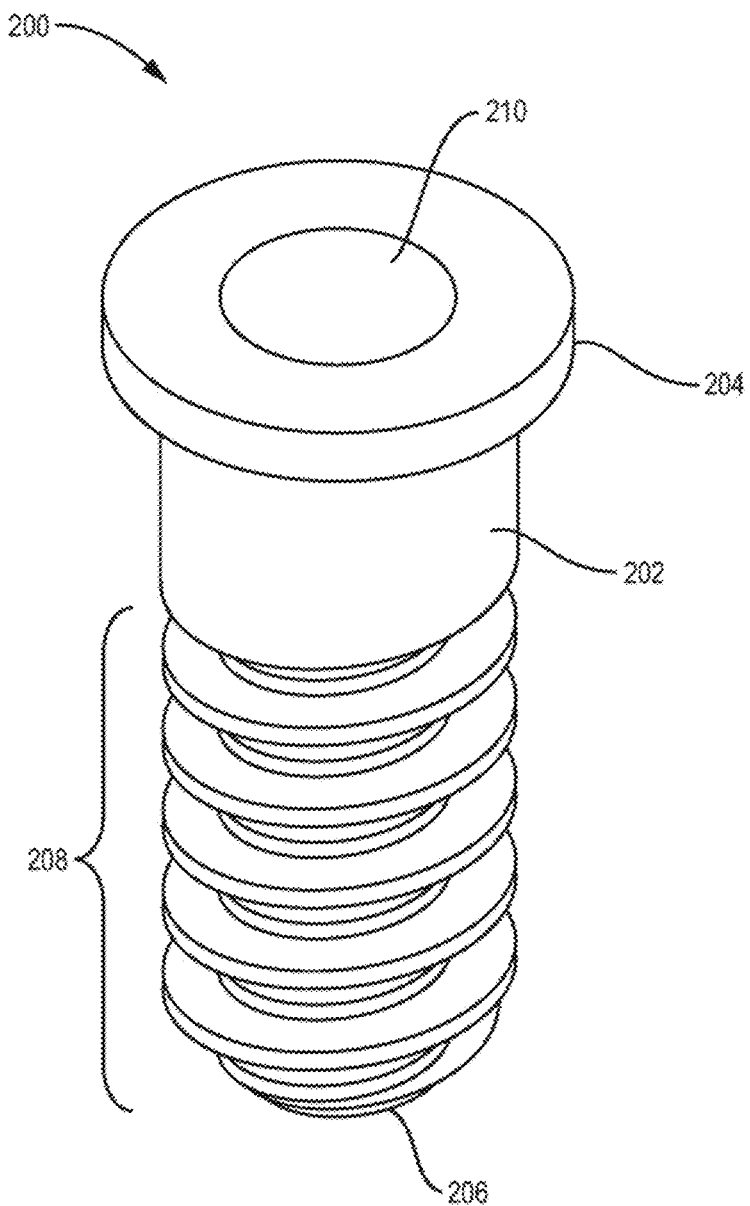
FIGS. 2A-2C illustrates an implant configured for constant, continuous, and controlled drug delivery in accordance with an embodiment of the present disclosure.
Figure 2B:
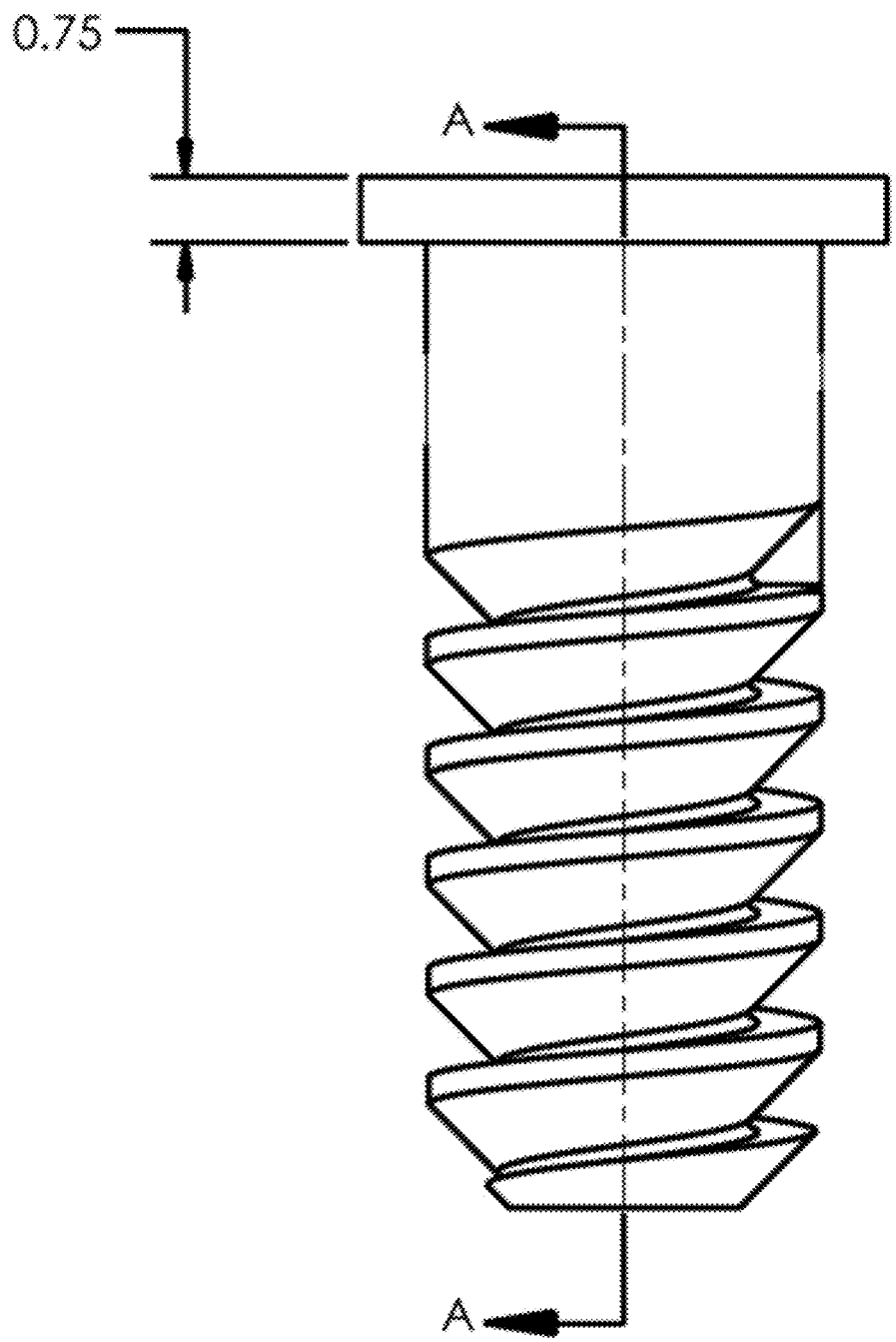
Figure 2C:
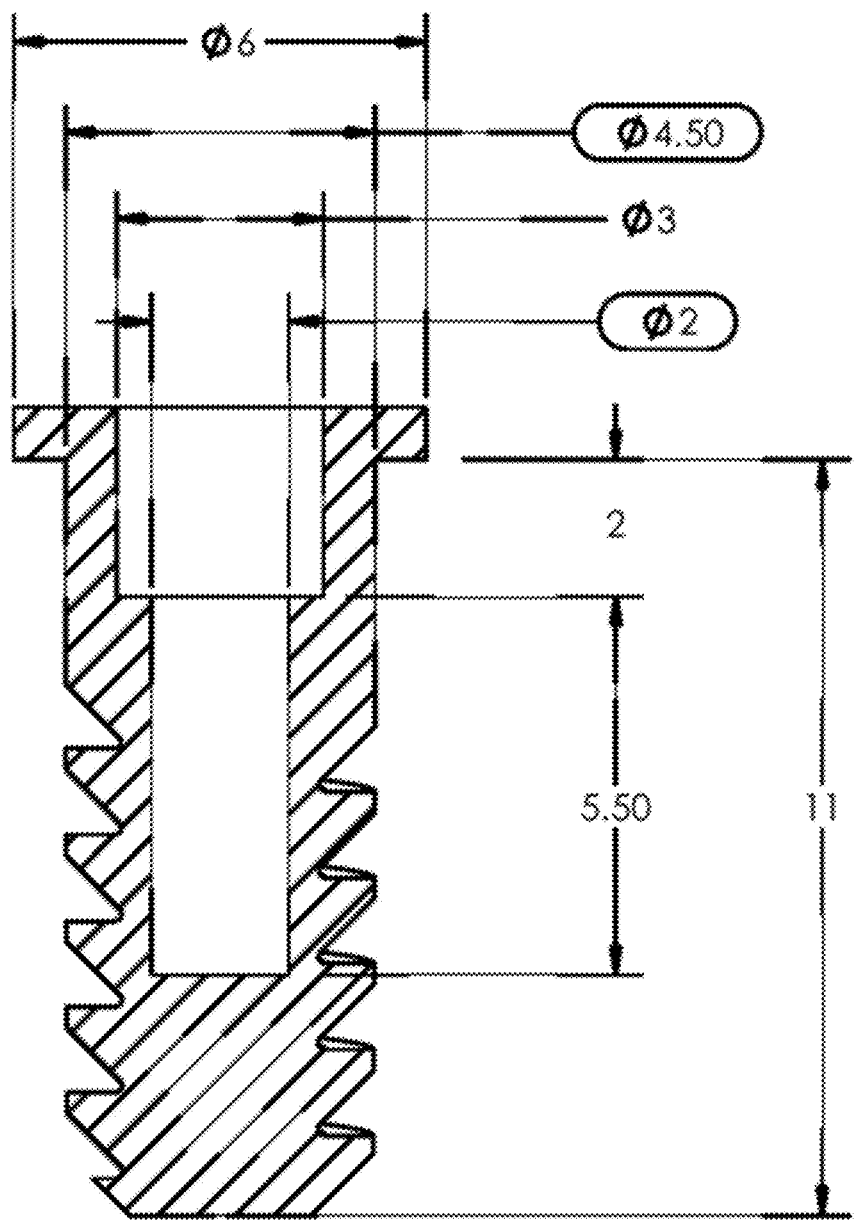

FIGS. 2A-2C illustrates an implant 200 configured for constant, continuous, and controlled drug delivery in accordance with an embodiment of the present disclosure. Similar to FIG. 1A, the implant 200 includes an elongate body 202 extending from a proximal end 204 to a distal end 206. In various embodiments, the proximal end 204 includes a flange extending radially outward from the elongate body 202. The flange can be configured with a disc shape, having a constant thickness around the circumference (e.g. devoid of any chamfer or beveled edges). Also, the flange can be sized with a larger diameter than the remainder of the implant, to serve as a collar such that a bottom surface of the flange engages the bone surface, with the circumferential edges and top surface of the flange spaced from, or not in contact with, the bone surface. In various embodiments, the distal end 206 includes a conical shape having a frustoconical (e.g., blunt) end. In various embodiments, the elongate body may include one or more threads 208 configured to secure the implant within a tissue (e.g., bone), similar to a screw. In various embodiments, the flange is designed to protrude from the elongate body so as to act as a stop to thereby prevent the implant from being inserted too deeply into the target tissue (e.g., bone). In preferred embodiments, the flange is circumferential and protrudes from the elongate body 102 by about 1 mm.

In various embodiments, the implant 200 further includes a bore 210 extending from the proximal end 204 at least partially into the elongate body 202. In various embodiments, similar to FIG. 1A, a payload (e.g., drug-polymer core, not shown) may be disposed within the bore. In various embodiments, the payload is disposed within the bore such that the entire cavity/volume of the bore is filled with the payload (e.g., the payload can, initially and before any eluting has occurred, be coplanar or flush with the upper surface of the flange 204 on the proximal end of the implant). In various embodiments, the exposed surface of the payload may be disposed below the flange (e.g., the top surface of the flange). In various embodiments, the exposed surface of the payload may be about 0.0 mm to about 5.0 mm below the surface of the flange. In various embodiments, the exposed surface of the payload may be substantially flat. Additionally, in some embodiments a temporary cover (e.g., biodegradable or bioerodible polymer) can be positioned over the payload to delay release of any therapeutic agent until a predetermined time, e.g., three weeks, after insertion into the bone. In various embodiments, the rings/threads may increase surface area of the implant within the bone to better secure the implant. In various embodiments, any other suitable structure as is known in the art may be used to increase surface area of the implant.

Figure 3A:
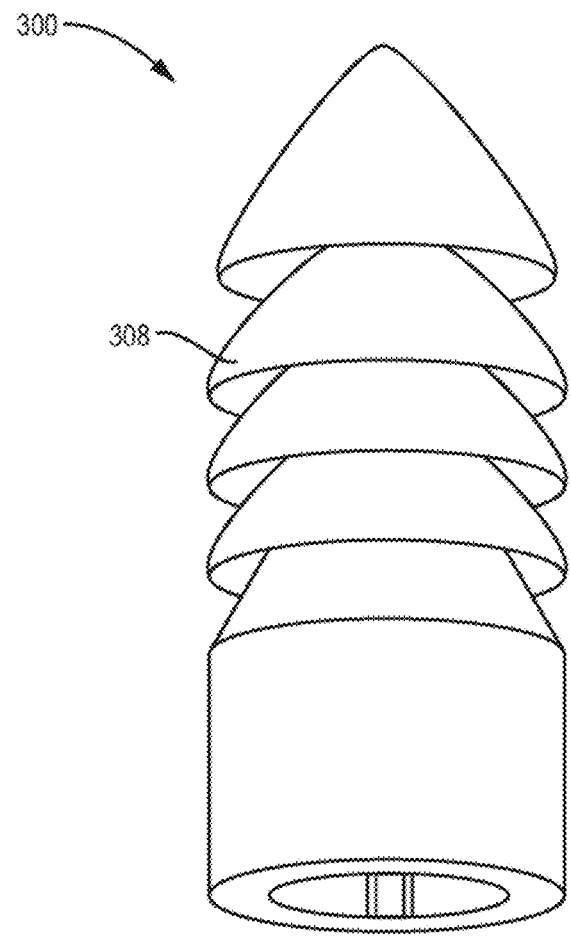
FIG. 3A illustrates an implant having interference rings in accordance with an embodiment of the present disclosure.
Figure 3B:
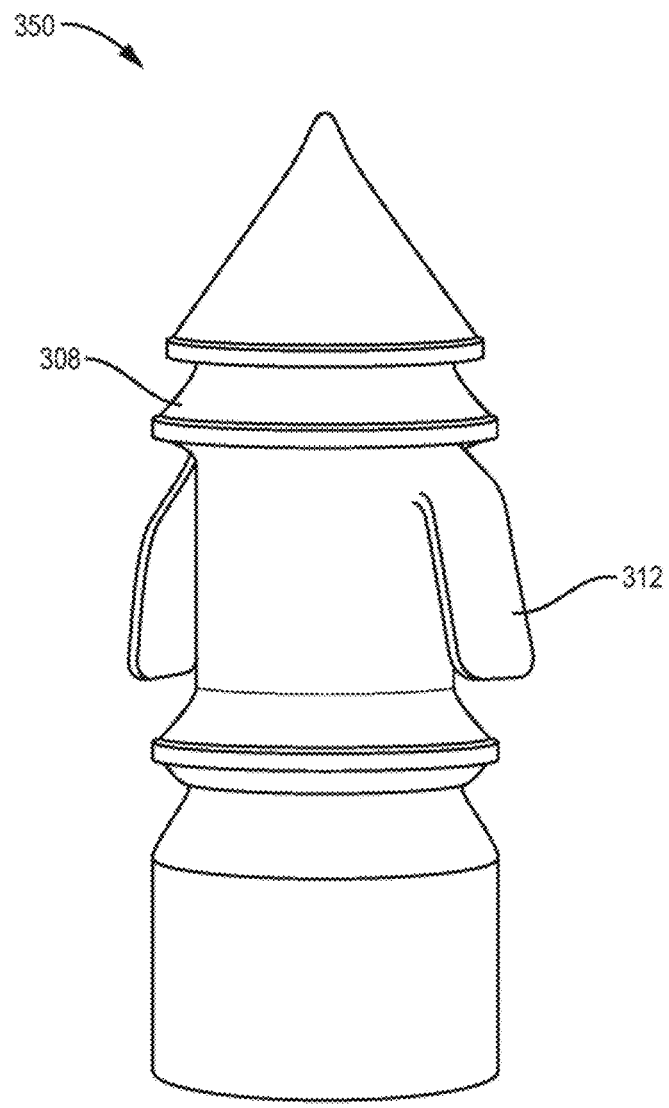
FIG. 3B illustrates an implant having interference rings and wing tabs in accordance with an embodiment of the present disclosure.

FIG. 3A illustrates an implant 300 having interference rings 308; the exemplary embodiment depicts rings of uniform shape/size, but additional/alternative shapes and sizes can be employed. In various embodiments, the rings can be formed with a constant angle or pitch relative to the shaft of the implant, e.g., avoiding the need for threaded insertion as required with helical threads. In various embodiments, the implant 300 shown in FIG. 3A is substantially similar to the implant 100 of FIG. 1A. FIG. 3B illustrates an implant 350 having interference rings and wing tabs 312. In various embodiments, the wing tabs 312 may be configured to secure the implant 350 within a tissue (e.g., bone) thereby preventing the implant from dislodging from the tissue.

Figure 4A:
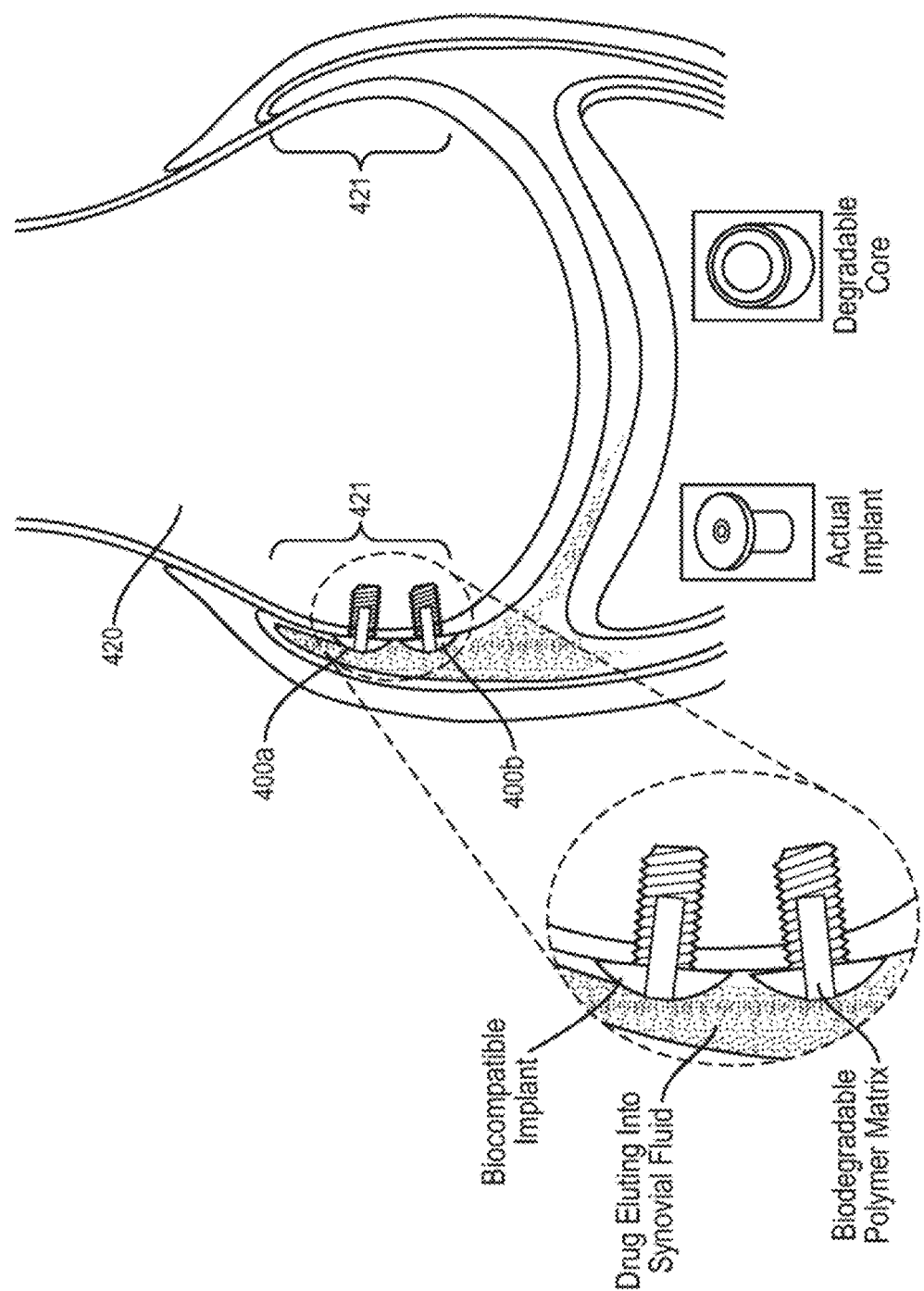
FIG. 4A illustrates a diagram of an implant fixed within a bone in accordance with an embodiment of the present disclosure.

FIG. 4A illustrates a diagram of implants 400a, 400b fixed within a bone 420. In particular, the bone 420 is a distal end of a femur. In various embodiments, the implant 400a, 400b may be secured within any suitable bone (e.g., femur, tibia, humerus, radius, ulna, pelvis, etc.) or within an implantable device such as an artificial hip or disc, where analgesic or anti-inflammatory therapeutic agents are needed to treat pain and/or inflammation in an articular joint. In various embodiments, the implant 400a, 400b may be secured in a non-load-bearing region 421 of the bone 420. For example, the implant 400a, 400b may be secured within a medial epicondyle or a lateral epicondyle of the femur.

Figure 4B:
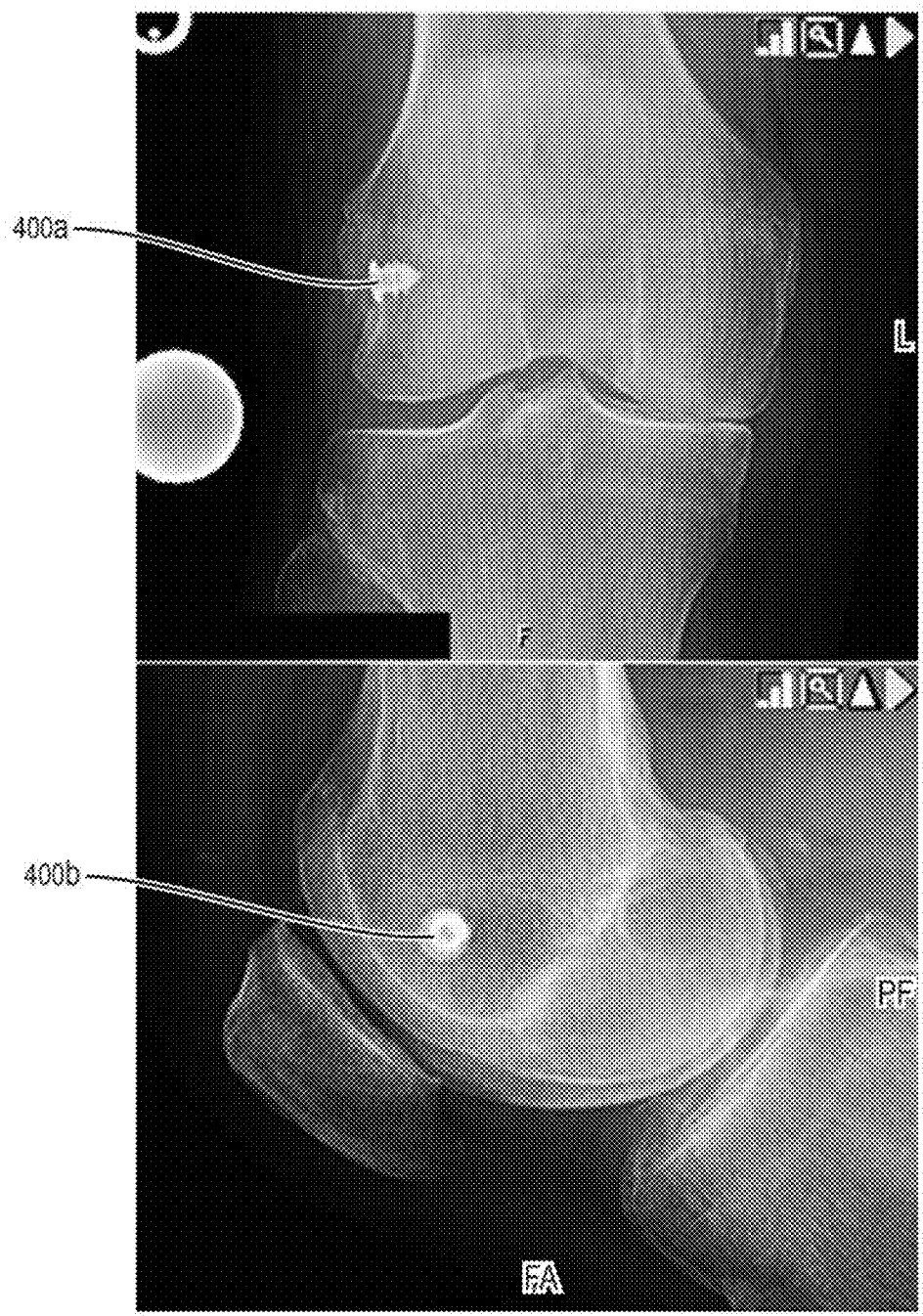
FIG. 4B illustrates an x-ray of an implant fixed within a bone in accordance with an embodiment of the present disclosure.

FIG. 4B illustrates two x-rays (lateral and frontal views) of an implant 400 fixed within a bone 420. As shown in FIG. 4B, the implant 400 is implanted in a non-load-bearing region of the femur.

FIG. 5A illustrates a table of treatments and length of effectiveness. In particular, effectiveness for NSAIDs is generally four to eight hours. Effectiveness for hyaluronic acid injections is eight to ten weeks. Effectiveness for a cortisone shot is six to twelve weeks. Effectiveness for triamcinolone acetonide extended-release injectable suspension (brand name Zilretta) is twelve weeks. Effectiveness for the implant described herein may be 26 weeks (e.g., 6 months) up to as high as 52 weeks (e.g., a year). In various embodiments, an implant may be designed to have an effectiveness for longer than 52 weeks.

Figure 5B:
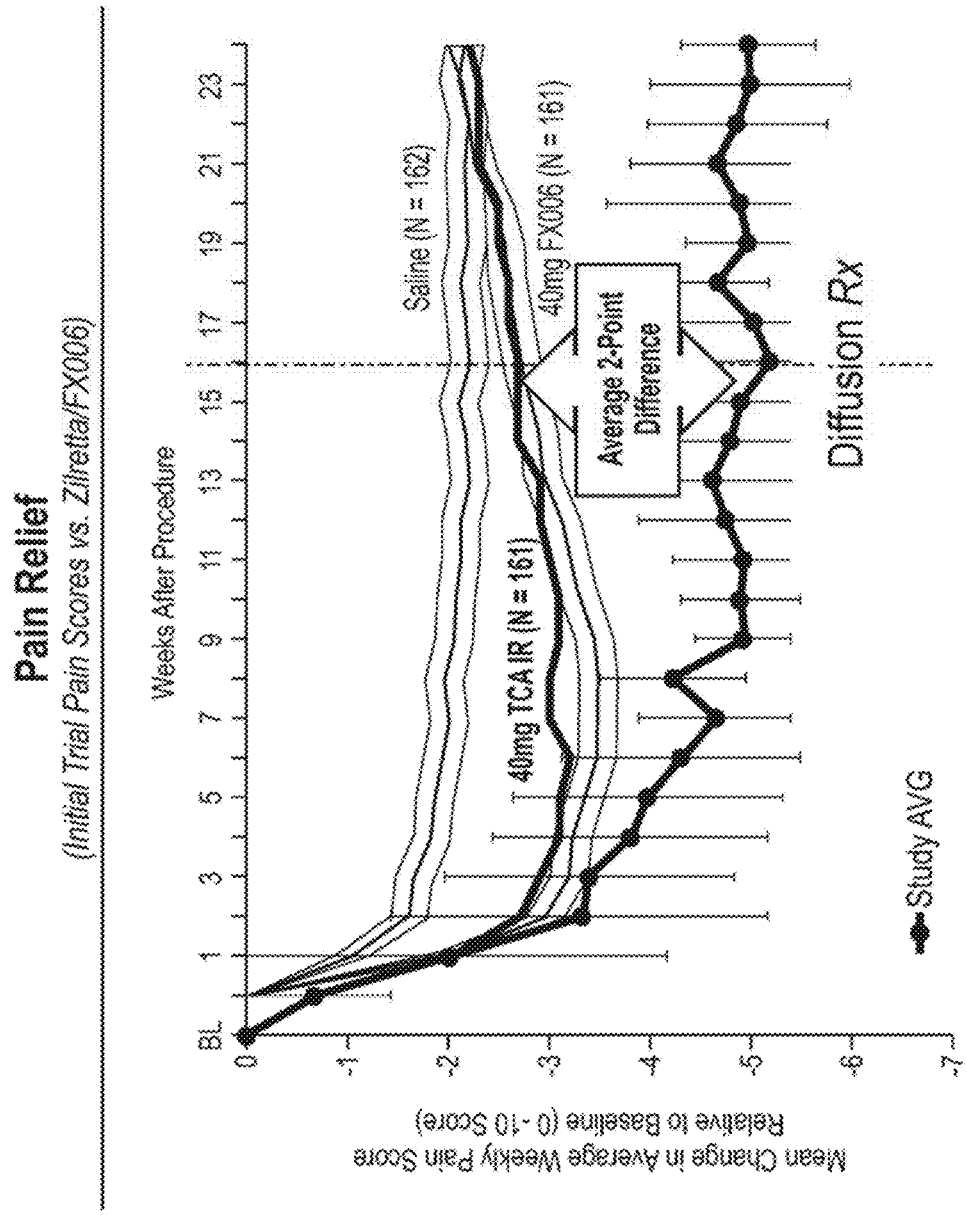
FIG. 5B illustrates a graph of pain relief from an implant in accordance with an embodiment of the present disclosure.

FIG. 5B illustrates a graph of pain relief from an implant. As shown in FIG. 5B, the implant described herein provides long-lasting relief for at least 24 weeks at an average difference of 2 points for mean change in average weekly pain score, significantly outperforming other known treatments (e.g., triamcinolone acetonide immediate release) and a control (saline).

Figure 5C:
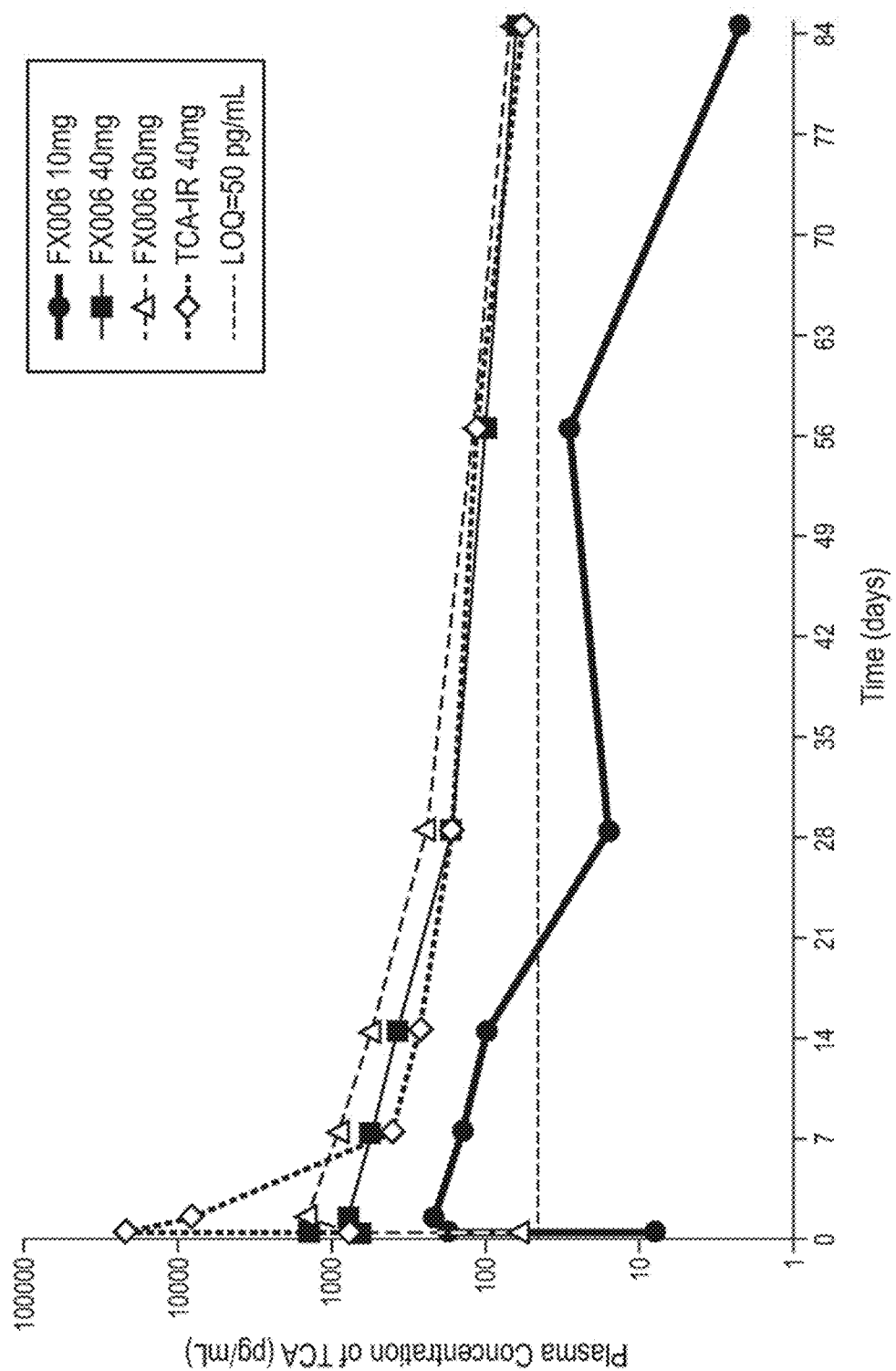
FIG. 5C-5D illustrate graphs of drug elution of pulse-dose single-injection treatments (FIG. 5C) and an implant (FIG. 5D) in accordance with an embodiment of the present disclosure.
Figure 5D:
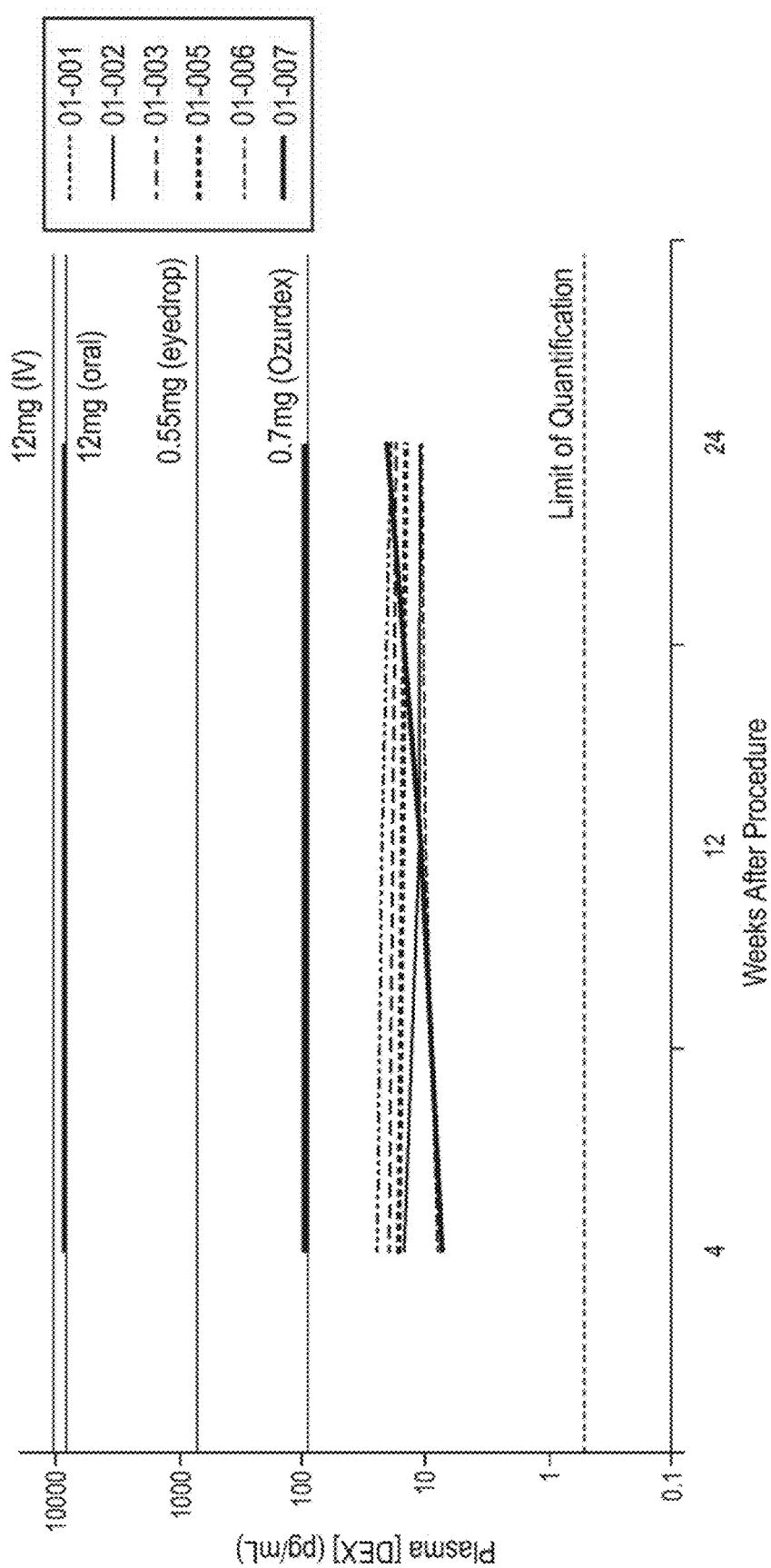

FIG. 5C-5D illustrate graphs of drug elution of pulse-dose treatments (FIG. 5C) and an implant (FIG. 5D). As shown in FIG. 5C, pulse-dose single-injection methods of treating intra-articular joint inflammation and/or pain have plasma concentration profiles that significantly decrease from time equals zero (i.e., when the pulse dose is administered) to 84 days out. These products "sustain" relief by releasing a large amount of drug upfront but those concentrations are quickly processed by the body and excreted. As shown in FIG. 5D, the plasma concentration profiles of the seven test subjects were substantially flat in all subjects over the entire trial period of 24 weeks. These data shown in FIG. 5D were obtained with implants that contained 5 mg dexamethasone with an in-vitro elution at a rate of approximately 10 μg/day. FIG. 5C illustrates first-order kinetics while FIG. 5D illustrates zero-order kinetics where the synovial cells are constantly and continuously coated with the therapeutic agent over time thus maintaining homeostasis.

In various embodiments, the implants of the present disclosure release a continuous, constant, and controlled low dosage of therapeutic agent. In various embodiments, the therapeutic agent may be released as the drug-polymer core bioerodes. In various embodiments, the therapeutic agent may be released as the drug-polymer core biodegrades. In various embodiments, this low dose of therapeutic agent effectively coats the cells whose job it is to maintain homeostasis within the articular joint to prevent any unwanted reactions (e.g., inflammation). In various embodiments, the continuous and constant dose of therapeutic agent (e.g., a corticosteroid) reduces inflammatory responses and prevents inflammation from starting back up. In various embodiments, the concentration of therapeutic agent released may be undetectable by commercial test assays.

Accordingly, the implants of the present disclosure may maintain a constant and continuous concentration in blood plasma over the course of 24 weeks with little variability, unlike pulse-dose injections. Moreover, corticosteroids have a time- and dose-dependent effect on joint tissues (e.g., articular cartilage), with beneficial effects occurring at low doses and durations and detrimental effects at high doses and durations. Clinically, beneficial effects are supported for intra-articular administration of corticosteroids, but the lowest effective dose should be used to minimize deleterious effects on cartilage morphology, histology, and viability. The implants of the present disclosure allow for a highly consistent (e.g., with little variability) blood plasma concentration and synovial concentration to be targeted, such as the lowest effective dose to prevent damage to intra-articular cartilage. The pulse-doses administered for injections, in contrast, may be high enough to cause damage to the surrounding tissues shortly after administration.

In various embodiments, beneficial effects of corticosteroids may occur at low doses and short durations (e.g., 8-12 mg/cumulative total dose) thereby resulting in increased cell growth and recovery from damage. In various embodiments, at higher doses and longer culture durations (e.g., 18-24 mg/cumulative total dose), corticosteroids may be associated with gross cartilage damage and chondrotoxicity. Literature demonstrates the complex effect methylpredisolone, dexamethasone, betamethasone, and hydrocortisone have on cartilage proteins (especially proteoglycan, type II collagen, aggrecan) through simultaneous mediation of the processes of protein production and breakdown. Methylprednisolone, dexamethasone, and hydrocortisone have demonstrated simultaneous mediation of both beneficial and detrimental upstream regulators of cartilage protein synthesis and breakdown, most notably the MMPs and tissue inhibitors of MMPs depending on dose and duration. In vivo studies of methylprednisolone, hydrocortisone, and triamcinolone also support significant cartilage protection at low doses.

In various embodiments, the implants of the present disclosure may take advantage of a biphasic dose-dependent effect of corticosteroids. In various embodiments, dose-dependent effects of corticosteroids on expression of matrix related genes in normal and cytokine treated intra-articular chondrocytes. In various embodiments, the constant and continuous release of the therapeutic agent described herein may provide a therapeutically-effective concentration of steroid without the negative effects of high concentrations of steroid (with logarithmic decline) that would be encountered after a pulse dose of steroid (e.g., after a corticosteroid injection). In various embodiments, the level of therapeutic agent never exceeds a predetermined threshold of drug. In various embodiments, measured blood levels of a therapeutic agent above the predetermined threshold may be associated (e.g., through clinical studies) with negative effects on a bodily tissue (e.g., cell strain, cell death, changes in cellular function, etc.). In various embodiments, the implants of the present disclosure provide a constant and continuous dose of a therapeutic agent within a therapeutically-effective window for the substantially the entire duration of the therapeutic lifespan of the implant. In various embodiments, the implants of the present disclosure maintain a blood level of therapeutic agent that is above a bottom threshold if a therapeutically-effective window but below a top threshold where, above this top threshold, negative effects on tissue (e.g., cytotoxicity) are known. In various embodiments, the therapeutically-effective window is a range of blood concentration of a therapeutic agent where, within this window, therapeutic effects on one or more bodily tissues are known clinically to occur.

Figure 6B:
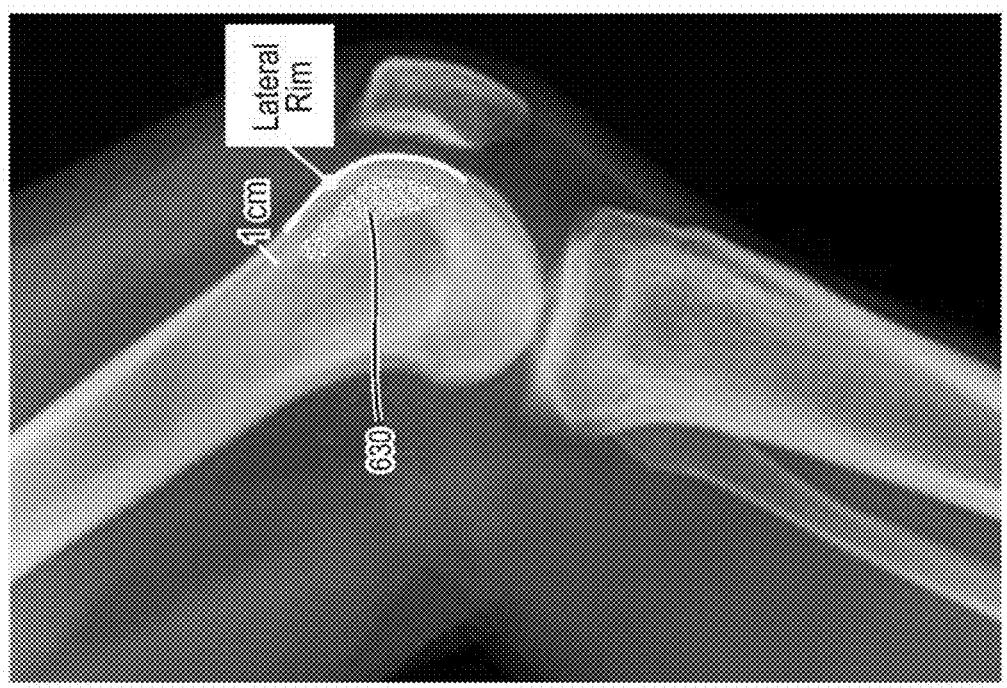
FIG. 6B illustrates a diagram of a safe implant zone in an x-ray of a knee joint in accordance with an embodiment of the present disclosure.
Figure 6A:
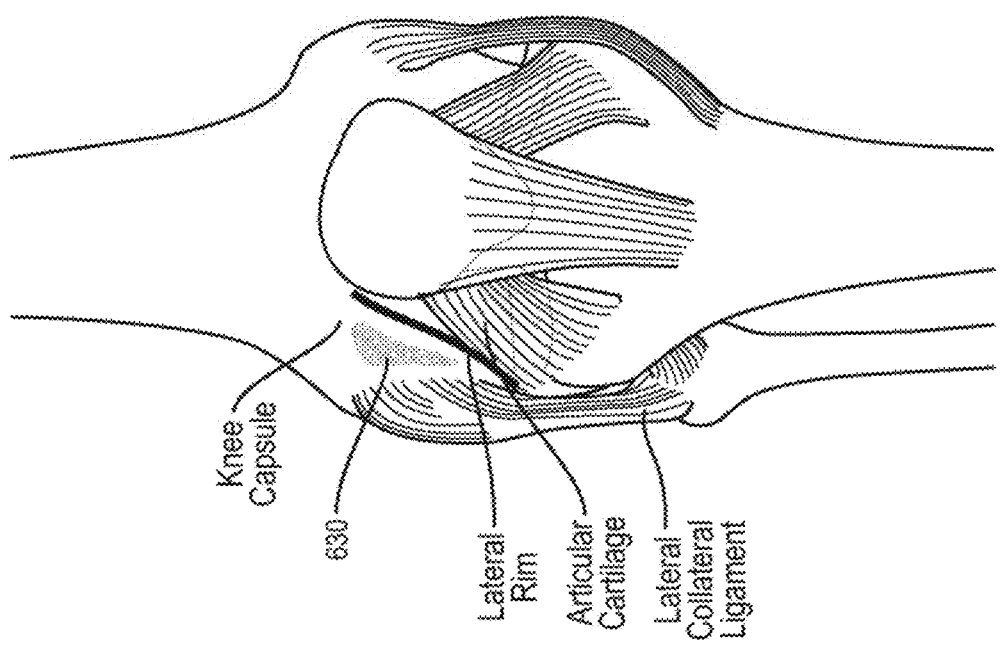
FIG. 6A illustrates a diagram of a safe implant zone in a knee joint in accordance with an embodiment of the present disclosure.

FIG. 6A illustrates a diagram of a safe implant zone 630 in a knee joint. In particular, FIG. 6A illustrates a safe zone 630 for implantation of one, or more, of the implant(s) in the lateral epicondyle of the femur. FIG. 6B illustrates a diagram of a safe implant zone 630 in an x-ray of a knee joint. Similar to the diagram of FIG. 6A, FIG. 6B shows a lateral view x-ray of a knee illustrating the safe zone in the lateral epicondyle. Exemplary safe zones include non-load-bearing regions in or around the articulation. The implantable device may be positioned, in certain applications, so that it releases the therapeutic into the articulation environment.

Figure 7:
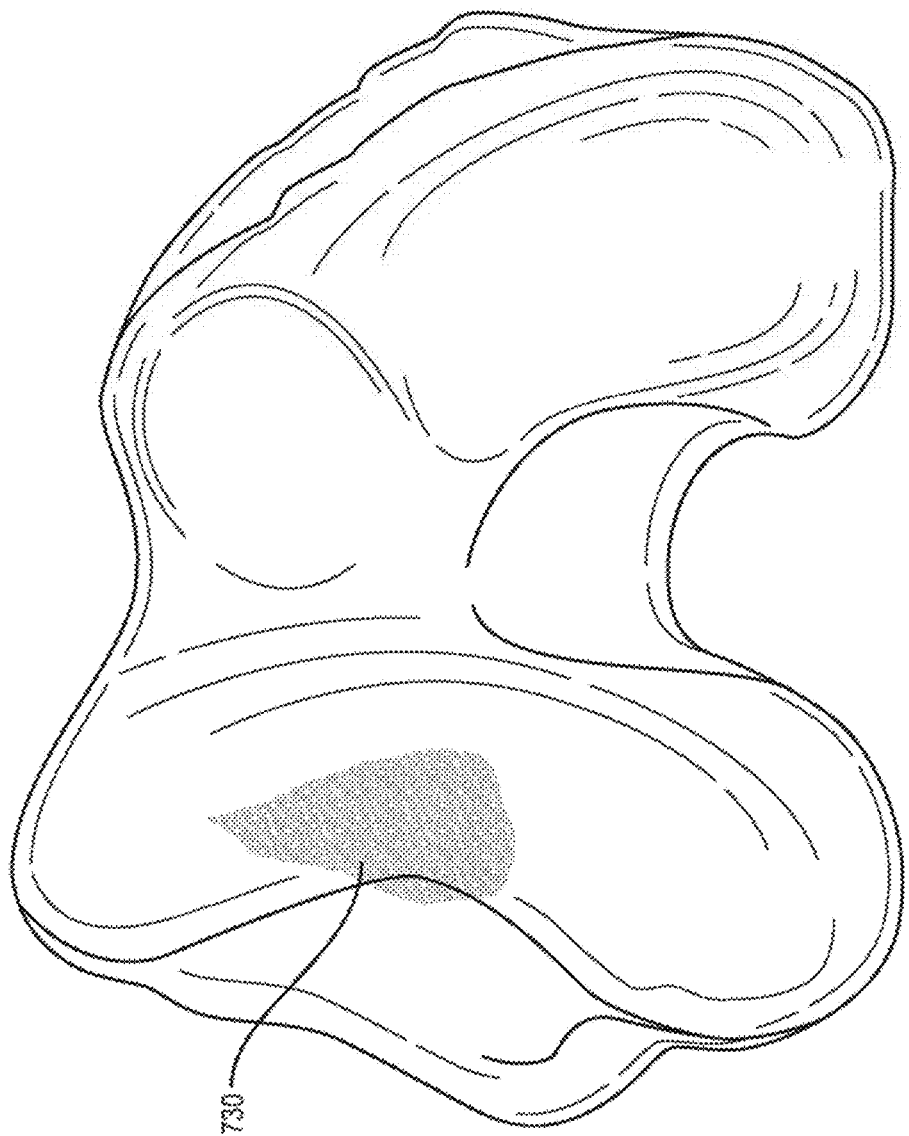
FIG. 7 illustrates a diagram of a safe implant zone in a knee joint in accordance with an embodiment of the present disclosure.

FIG. 7 illustrates a diagram of a safe implant zone 730 in a knee joint. In particular, FIG. 7 shows a bottom-up view of a femur and illustrates approximately where the implant would reside after implantation in a non-load-bearing region of the femur.

Figure 8:
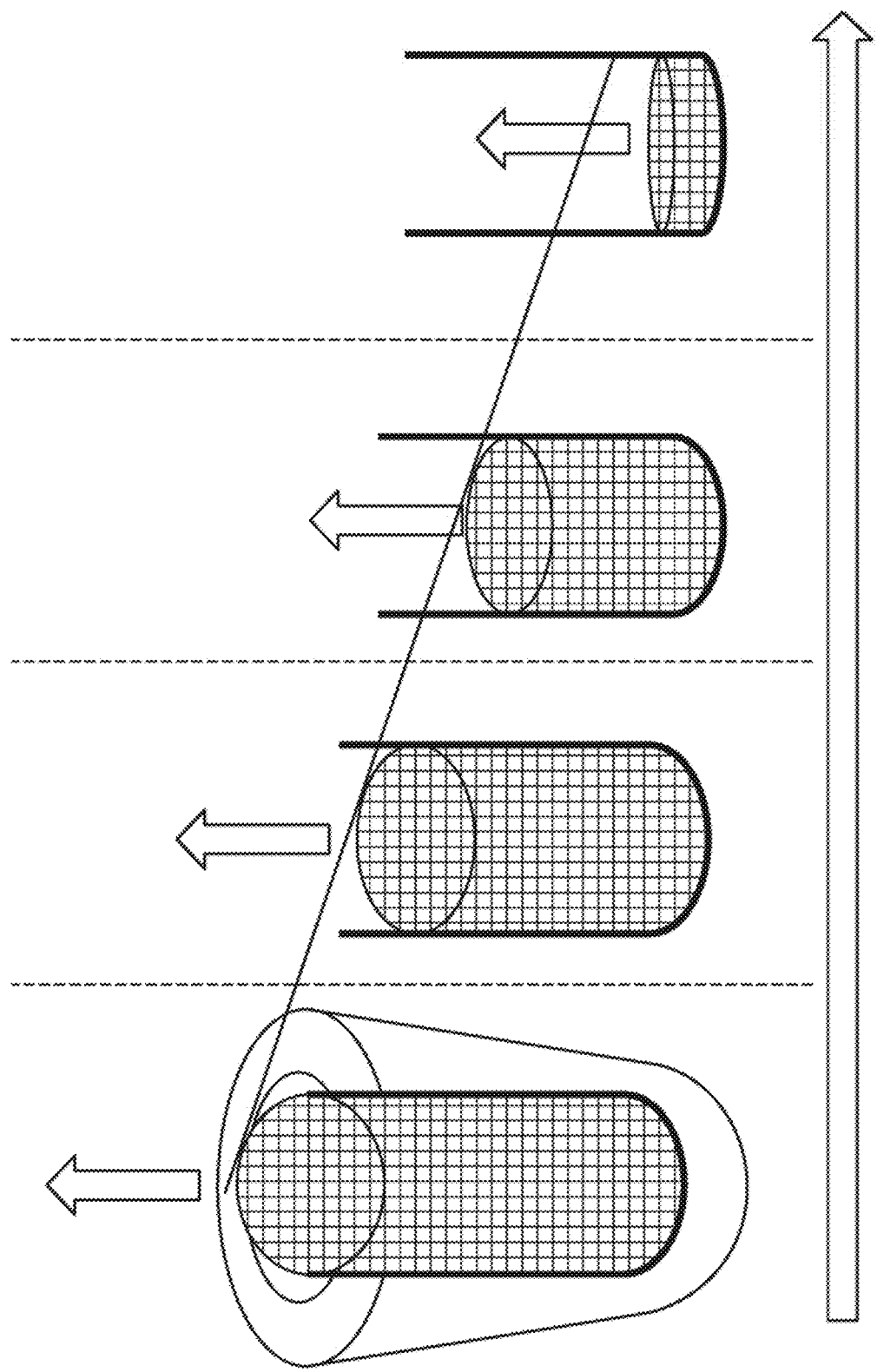
FIG. 8 illustrates a diagram of therapeutic agent elution over time in accordance with an embodiment of the present disclosure.

FIG. 8 illustrates a diagram of therapeutic agent elution over time in accordance with an embodiment of the present disclosure. In particular, FIG. 8 illustrates elution of a therapeutic agent (e.g., a drug contained within a polymer matrix). In various embodiments, the surface area of elution (i.e., the exposed portion of the payload within the bore) remains constant throughout the duration of treatment. In various embodiments, the sides of the payload implant are sealed from synovial fluid exposure and only the top circular area portion is exposed to the bodily environment. In various embodiments, the drug elutes at a constant rate with a constant surface area, thus providing a stable, continuous, and constant level of drug over time in the immediate bodily area surrounding the implant. In various embodiments, the therapeutic agent may be mixed with any suitable matrix, such as a polymer matrix, that is configured to release a constant and continuous amount of the therapeutic agent after implantation in a tissue. In various embodiments, the matrix may be bioerodible. In various embodiments, the matrix may be biodegradable. In various embodiments, the matrix may be polylactic acid (PLA), trimethylene carbonate, polycaprolactone, polybutylene succinate, polybutylene succinate adipate, aliphatic—aromatic copolyesters, polybutylene adipate/terephthalate, and polymethylene adipate/terephthalate. In certain embodiments, the polymer matrix may be polyvinyl alcohol.

In various embodiments, the payload may include only a therapeutic agent (i.e., without a matrix).

Figure 9:
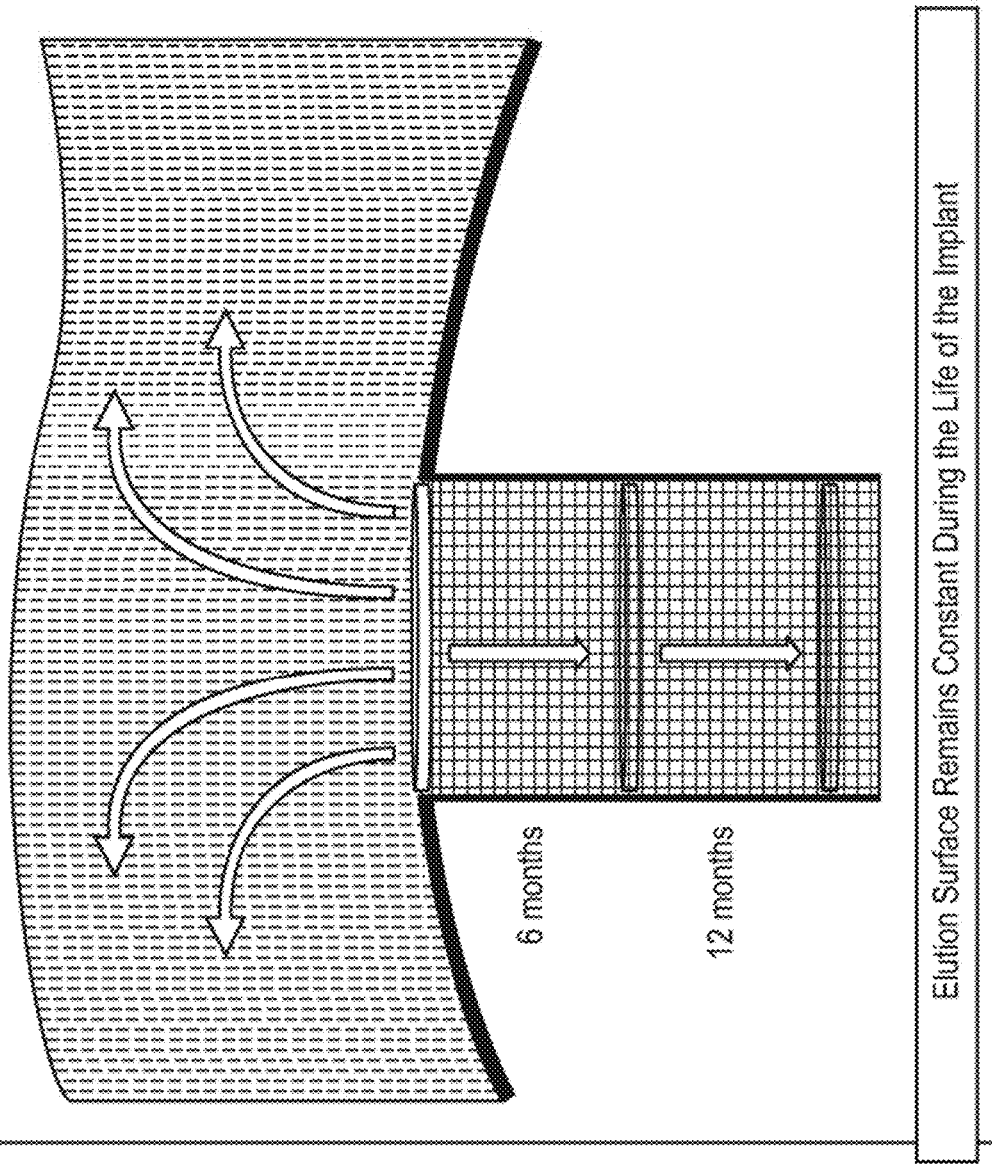
FIG. 9 illustrates a diagram of therapeutic agent elution over time in accordance with an embodiment of the present disclosure.

FIG. 9 illustrates a diagram of therapeutic agent elution over time in accordance with an embodiment of the present disclosure. As shown in FIG. 9, the exposed portion of the payload disposed within the bore of the implant, called the elution surface, remains substantially constant. In various embodiments, the elution surface remains substantially constant throughout the life of the implant. Release of the drug from the exposed elution surface (e.g., via bioerosion of a drug-polymer core) is rate-limiting and therefore allows for greater control of drug elution compared to other known methods in the art, such as, for example, diffusion of a drug through a non-erodible polymer and out of an exposed surface (as described in U.S. Pat. No. 6,936,270).

Figure 10A:
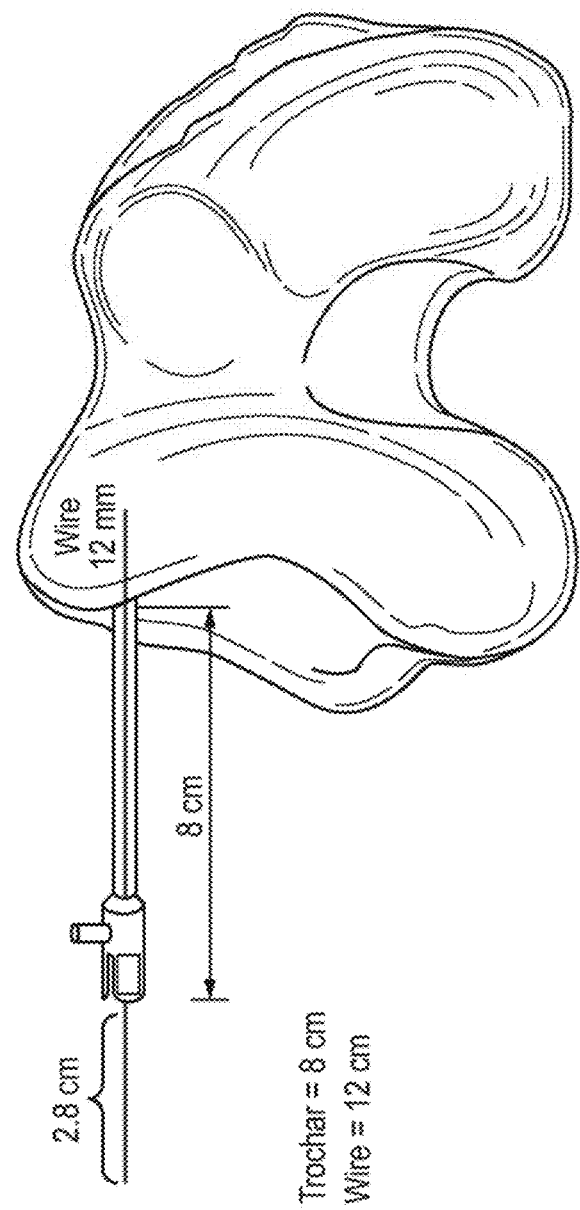
FIGS. 10A-10E illustrates a method for implanting a constant and continuous drug-eluting implant in a knee joint in accordance with an embodiment of the present disclosure.
Figure 10B:
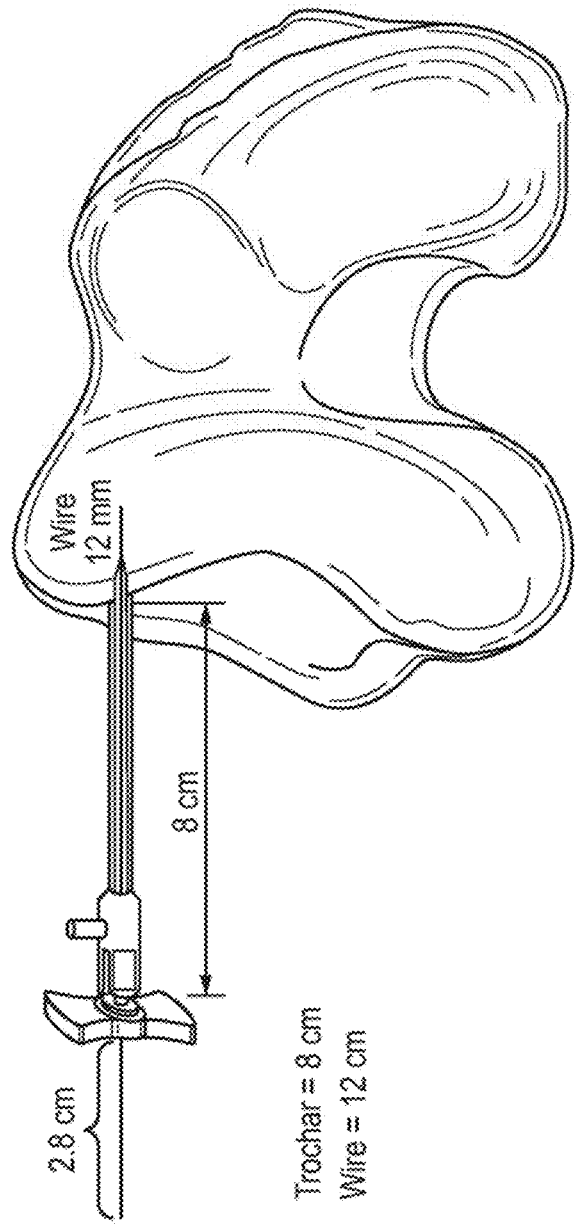
Figure 10C:
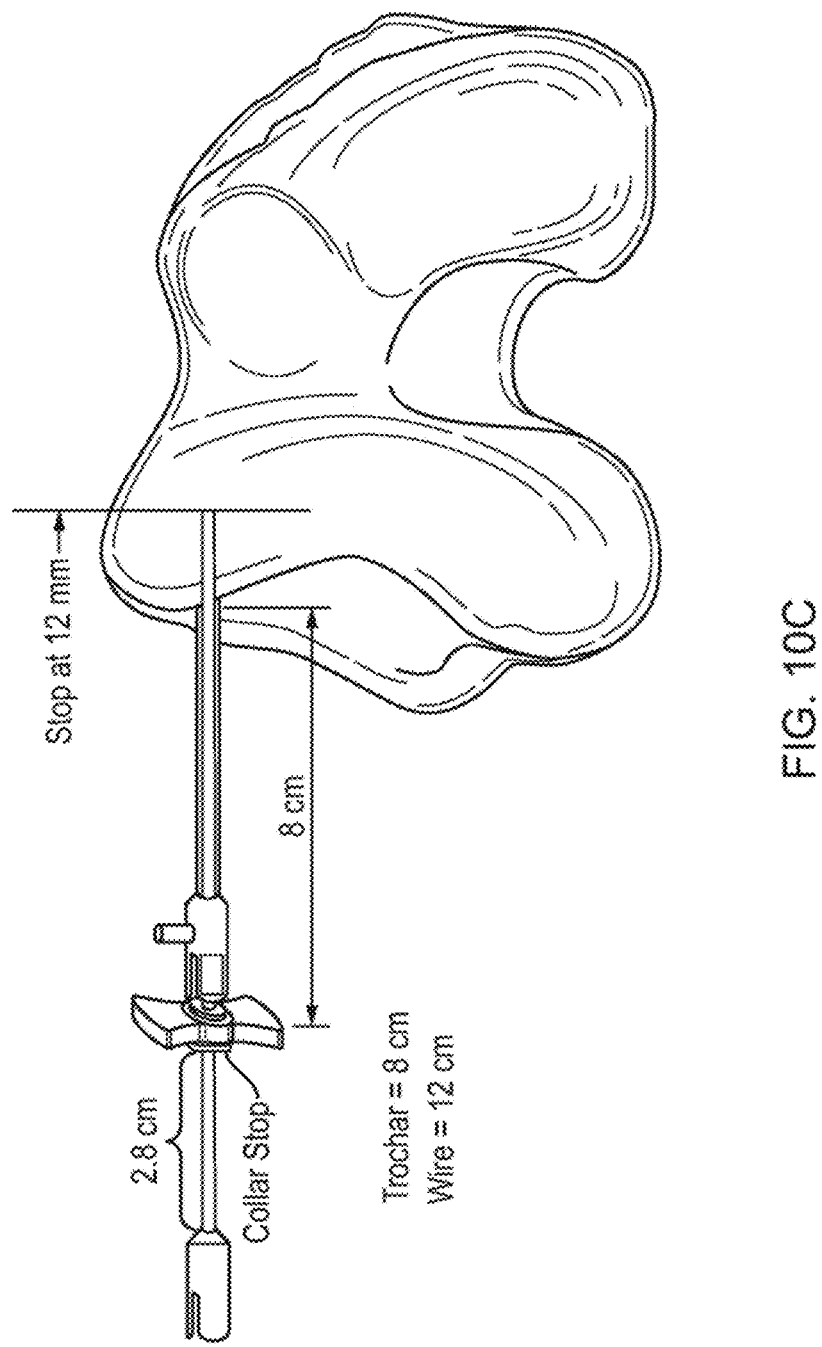
Figure 10D:
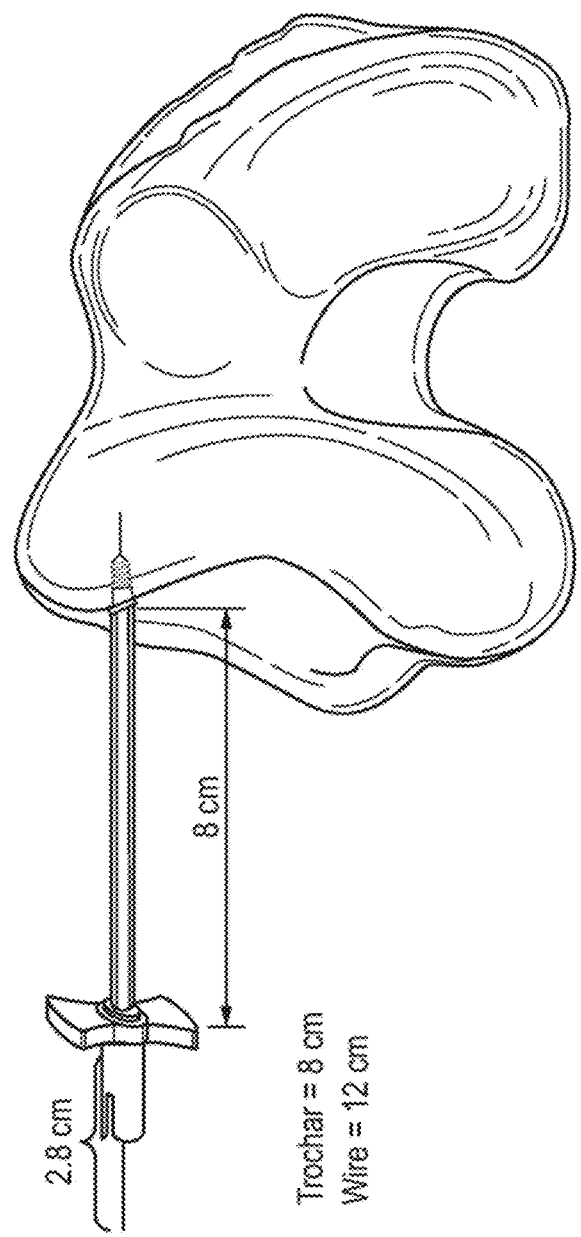
Figure 10E:
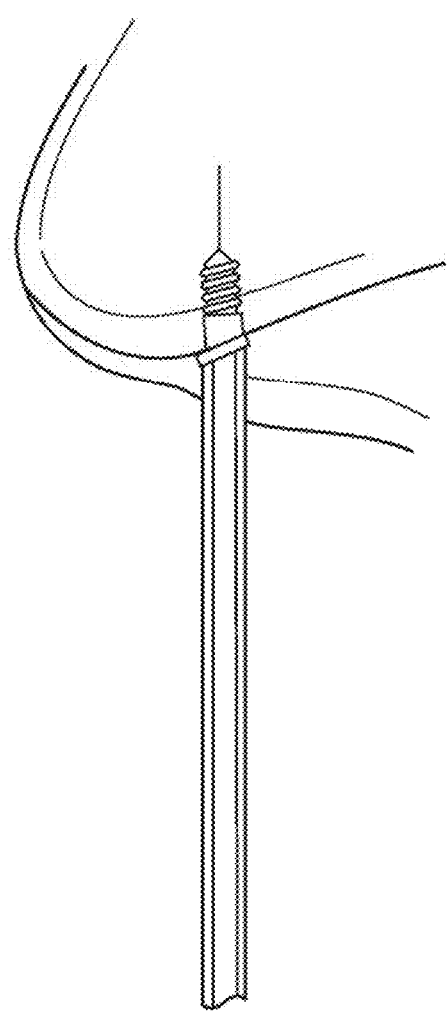

FIGS. 10A-10E illustrates a method for implanting a constant and continuous drug-eluting implant in a knee joint in accordance with an embodiment of the present disclosure. In FIG. 10A, a percutaneous incision is made in the layers of tissue to expose the periosteum of the femur. In FIG. 10B, a trocar is inserted into the incision. In FIG. 10C, the trocar is used to form a hole through the periosteum and into the cortical bone. In various embodiments, a collar-stop may be used (e.g., attached to the trocar or integrally formed therewith) to accurately gauge depth of the formed hole in the bone. In various embodiments, the preferred depth of the hole in the bone is about 12 mm. In FIGS. 10D-10E, the constant and continuous drug-eluting implant is inserted through the percutaneous incision and secured within the hole formed in the bone. In various embodiments, the implant may be secured within the hole via one or more impulse forces, for example, via a hammer, applicator, or mallet. In various embodiments, a trocar may be used for positioning on the surface of the safe zone (e.g., periarticular bone).

In various embodiments, a cannula with a trocar may be used to position the cannula for pilot-guide wire insertion and confirmation of placement. In various embodiments, after positioning the cannula, a cannulated drill may be used to prepare the site for device insertion. In various embodiments, a drill with a stop may be used to form a hole within the bone. In various embodiments, a step drill may be used to provide assisted insertion of the implant.

Figure 11A:
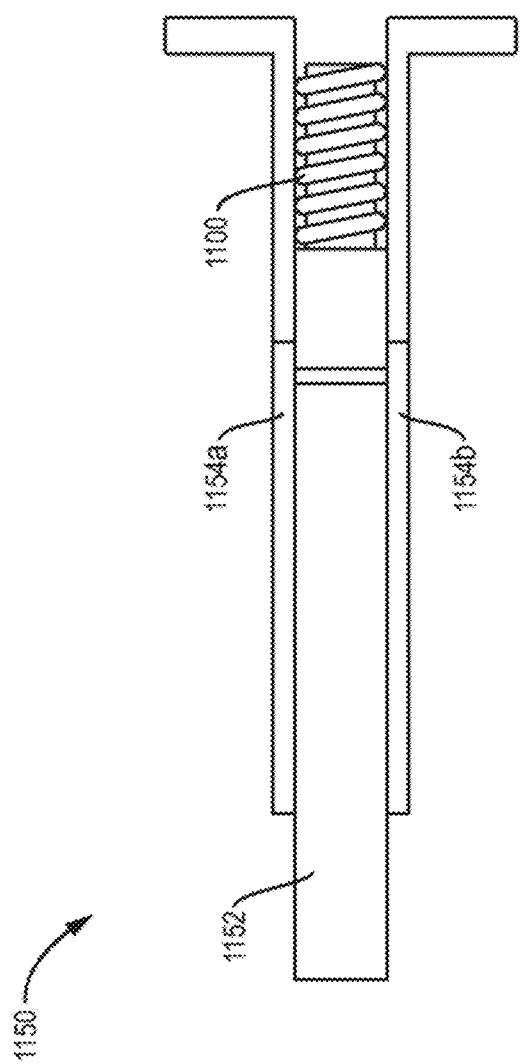
FIGS. 11A-11C a process of opening sterile packaging of an exemplary delivery device having an implantable device in accordance with an embodiment of the present disclosure.
Figure 11B:
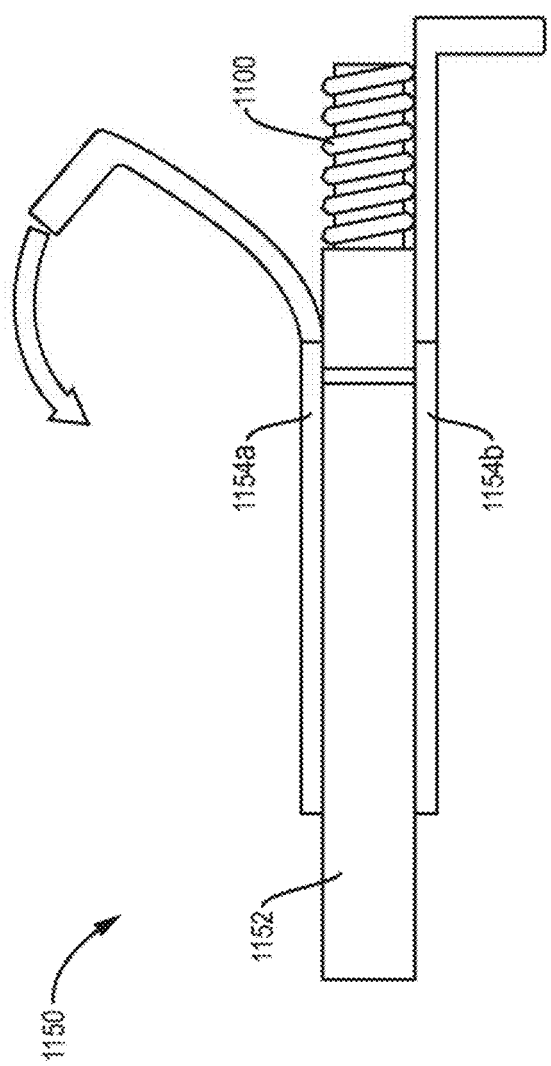
Figure 11C:
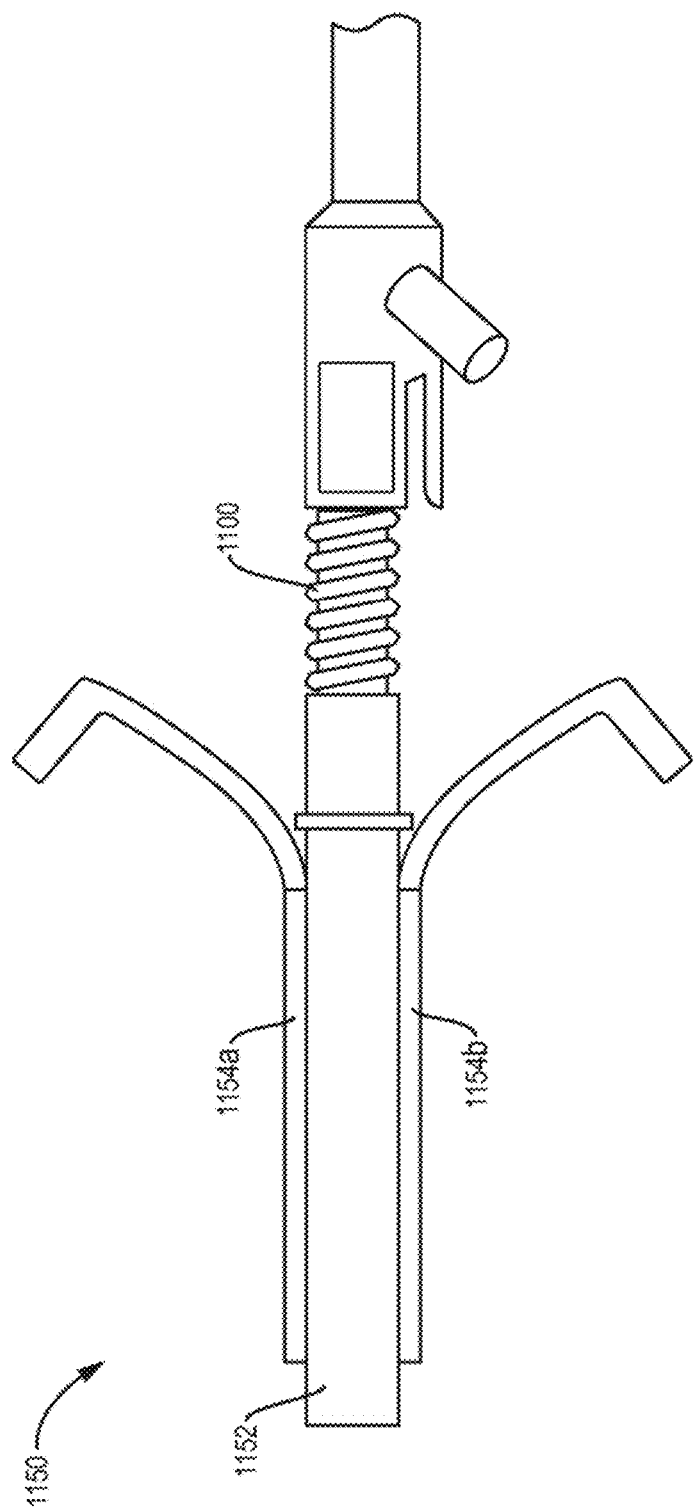

FIGS. 11A-11C illustrates a process of opening sterile packaging of an exemplary delivery device 1150 having an implantable device 1100. The delivery device 1150 is configured to deliver an implantable device 1100, such as the delivery devices described above. In various embodiments, the delivery device includes a rod 1152. In various embodiments, the sterile packaging is configured to contain at least a portion (e.g., all) of the rod 1152 and fully enclose the implantable device 1100. In various embodiments, the sterile packaging includes a first peelable side 1154*a* and a second peelable side 1154*b*. In various embodiments, the sterile packaging may include any suitable number of peelable sides to allow for sterile removal of the delivery device 1150. In various embodiments, the sterile packaging includes a shrink-wrapped peel-pack. In various embodiments, the sterile packaging includes a stock keeping unit (SKU) number uniquely identifying the particular implant. In various embodiments, the sterile packaging includes manufacturing information, such as date manufactured, unit number, manufacturing line identifier, manufacturer location, other manufacturer information, etc. As shown in FIG. 11A, the sterile packaging seals the delivery device 1150 and the implantable device 1150. As shown in FIG. 11B, a first step to open the packaging includes peeling back the first side 1154*a* of the sterile packaging. As shown in FIG. 11C, a second step to open the packaging includes peeling back the second side 1154*b* of the sterile packaging to fully expose the sterile implantable device 1100.

EXAMPLE

Six patients with severe osteoarthritis of the knee were recruited into a trial. All patients were candidates for total knee replacement surgery. In this 6-month trial patients received an intra-articular implant providing sustained release of Dexamethasone (5 mg). Efficacy was determined by comparison of pain scores as shown in Table 1 (obtained by questionnaire completed pre-op and twice each week for 6 months) and changes in quality of life (assessed by KOOS-JR obtained pre-operatively and at weeks 1, 2, 4, 8, 12, and 24). Blood samples were periodically taken to measure systemic exposure. After completion of the study, patients were followed for up to an additional 18 months where possible (24 months total). In Table 1, "strict" is defined as having greater than a 2 point pain reduction and greater than 50% pain reduction (FDA).

TABLE 1

| Pain Efficacy | | | | |
|---|---|---|---|---|
| "Strict" Responders via Pain | Wk 4 | Wk 8 | Wk 12 | Wk 24 |
| IND124256 | 67% | 100% | 100% | 100% |

The low dose implants were highly effective in this study of patients with severe OA of the knee, all of whom (by protocol) were candidates for total knee replacement surgery. All patients were "strict responders." The implants were safe, there were no reports of SAEs. Although this was a 6 month study follow-up continued for up to 24 months. At 24 months only one patient needed TJA since receiving an implant and one patient has had an IA steroid injection. In various embodiments, a drug eluting core may be placed in a modified bone screw. In various embodiments, the implants described herein can be percutaneously inserted during an office visit.

What is claimed is:

1. An intra-articular implant sized and configured to be implanted in a periarticular region of a joint, the intra-articular implant comprising:
   an elongate body extending from a proximal end to a distal end, the elongate body comprising a bone anchor;
   a flange disposed at the proximal end and extending radially outwards from the elongate body, the flange configured to be exposed to synovial fluid of the joint;
   a bore extending from an opening at the proximal end into the elongate body, wherein the bore comprises an inner surface where it extends into the elongate body;
   one or more fixation members disposed on an outer surface of the elongate body; and
   a payload disposed within the bore, wherein the payload comprises a therapeutic agent configured to elute constantly and continuously over a predetermined time period,
   wherein the payload erodes during elution, wherein a substantially constant surface area of an exposed portion of the payload is present throughout elution, and wherein the inner surface of the bore of the intra-articular implant is sealed and only the opening at the proximal end of the bore exposes the constant surface area of the exposed portion of the payload,
   wherein the bore comprises a depth of about 0.5 mm to about 12 mm,
   wherein the depth of the bore is larger than a maximum height of the flange,
   wherein a length from the proximal end to the distal end is about 7 mm to about 12 mm, wherein the substantially constant surface area of the exposed portion of the payload is substantially planar with a plane of the flange throughout elution, wherein, except for the opening at the proximal end, the intra-articular implant is devoid of any means exposing payload to bodily environment, wherein the intra-articular implant is configured to achieve substantially zero-order kinetic drug delivery in said periarticular region of the joint.

2. The intra-articular implant of claim 1, wherein the one or more fixation members comprises one or more interference rings disposed along the elongate body.

3. The intra-articular implant of claim 1, wherein the one or more fixation members comprises two or more wing tabs disposed along the elongate body.

4. The intra-articular implant of claim 3, wherein the two or more wing tabs are disposed opposite one another.

5. The intra-articular implant of claim 1, wherein the one or more fixation members comprises threads disposed along the elongate body.

6. The intra-articular implant of claim 1, wherein the distal end comprises a conical shape.

7. The intra-articular implant of claim 1, wherein the distal end comprises a frustoconical shape.

8. The intra-articular implant of claim 1, wherein a diameter of the bore is about 0.5 mm to about 9.5 mm.

9. The intra-articular implant of claim 1, wherein the bore extends only partially into the elongate body.

10. The intra-articular implant of claim 1, wherein the elongate body comprises a first diameter and the flange comprises a second diameter.

11. The intra-articular implant of claim 10, wherein the second diameter is larger than the first diameter.

12. The intra-articular implant of claim 10, wherein the first diameter is about 1.0 mm to about 10.0 mm.

13. The intra-articular implant of claim 10, wherein the second diameter is about 1.25 mm to about 12.0 mm.

14. The intra-articular implant of claim 1, wherein the payload is in direct contact with the inner surface of the bore.

15. The intra-articular implant of claim 1, wherein the payload is configured to elute the therapeutic agent constantly and continuously for about six months.

16. The intra-articular implant of claim 1, wherein the payload is configured to elute the therapeutic agent constantly and continuously for about seven months.

17. The intra-articular implant of claim 1, wherein the payload is configured to elute the therapeutic agent constantly and continuously for about eight months.

18. The intra-articular implant of claim 1, wherein the payload is configured to elute the therapeutic agent constantly and continuously for about nine months.

19. The intra-articular implant of claim 1, wherein the payload is configured to elute the therapeutic agent constantly and continuously for about ten months.

20. The intra-articular implant of claim 1, wherein the payload is configured to elute the therapeutic agent constantly and continuously for about eleven months.

21. The intra-articular implant of claim 1, wherein the payload is configured to elute the therapeutic agent constantly and continuously for about a year.

22. The intra-articular implant of claim 1, wherein the payload is configured to elute the therapeutic agent constantly and continuously for at least a year.

23. The intra-articular implant of claim 1, wherein the therapeutic agent comprises a corticosteroid.

24. The intra-articular implant of claim 23, wherein the corticosteroid comprises dexamethasone.

25. The intra-articular implant of claim 1, wherein the elongate body comprises titanium.

26. The intra-articular implant of claim 1, wherein the elongate body comprises polyetherketoneketone (PEKK).

27. The intra-articular implant of claim 1, wherein the elongate body comprises polyether ether ketone (PEEK).

28. The intra-articular implant of claim 1, wherein the therapeutic agent is configured to elute constantly and continuously at an amount that is above a predetermined lower threshold and does not exceed a predetermined upper threshold.

29. A method of treating an inflammatory condition, the method comprising:
    implanting the intra-articular implant of claim 1 into a bone, thereby allowing the payload to elute the therapeutic agent into an intra-articular space at a constant and continuous rate for at least a year.

30. A method of treating an inflammatory condition, the method comprising:
    providing the intra-articular implant of claim 1;
    forming a hole in a bone;
    inserting the intra-articular implant into the formed hole thereby securing the intra-articular implant in the bone.

31. The method of claim 30, wherein the hole is formed using a drill.

32. The method of claim 30, wherein the hole has a depth of about 8 mm to about 16 mm.

33. The method of claim 30, wherein the hole has a depth of about 12 mm.

34. The method of claim 30, wherein the hole is formed in a non-load-bearing portion of the bone.

35. The method of claim 30, wherein the bone is a femur.

36. The method of claim 35, wherein the hole is formed in a periarticular region.

* * * * *

UNITED STATES PATENT AND TRADEMARK OFFICE
CERTIFICATE OF CORRECTION

| | |
|---|---|
| PATENT NO. | : 11,980,701 B2 |
| APPLICATION NO. | : 17/576635 |
| DATED | : May 14, 2024 |
| INVENTOR(S) | : Hotchkiss et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 58 days.

Signed and Sealed this
Thirty-first Day of December, 2024

Derrick Brent
*Acting Director of the United States Patent and Trademark Office*